United States Patent
Gupta et al.

(10) Patent No.: US 10,047,368 B2
(45) Date of Patent: Aug. 14, 2018

(54) ZEA MAYS REGULATORY ELEMENTS AND USES THEREOF

(71) Applicant: Dow AgroSciences LLC, Indianapolis, IN (US)

(72) Inventors: Manju Gupta, Carmel, IN (US); Navin Elango, Indianapolis, IN (US); Karthik N. Muthuraman, Boston, MA (US); Jeffrey Beringer, Carmel, IN (US); Sara Bennett, Indianapolis, IN (US); Huixia Wu, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 41 days.

(21) Appl. No.: 14/514,837

(22) Filed: Oct. 15, 2014

(65) Prior Publication Data

US 2015/0106978 A1   Apr. 16, 2015

Related U.S. Application Data

(60) Provisional application No. 61/890,904, filed on Oct. 15, 2013.

(51) Int. Cl.
  *C12N 15/82* (2006.01)
  *C12N 15/113* (2010.01)

(52) U.S. Cl.
  CPC ........ *C12N 15/8216* (2013.01); *C12N 15/113* (2013.01); *C12N 15/8222* (2013.01); *C12N 15/8237* (2013.01)

(58) Field of Classification Search
  None
  See application file for complete search history.

(56) References Cited

U.S. PATENT DOCUMENTS

| | | |
|---|---|---|
| 4,683,195 A | 7/1987 | Mullis et al. |
| 5,004,863 A | 4/1991 | Umbeck |
| 5,015,580 A | 5/1991 | Christou et al. |
| 5,159,135 A | 10/1992 | Umbeck |
| 5,188,960 A | 2/1993 | Payne et al. |
| 5,302,523 A | 4/1994 | Coffee et al. |
| 5,380,831 A | 1/1995 | Adang et al. |
| 5,384,253 A | 1/1995 | Krzyzek et al. |
| 5,464,765 A | 11/1995 | Coffee et al. |
| 5,508,184 A | 4/1996 | Negrutiu et al. |
| 5,538,880 A | 7/1996 | Lundquist et al. |
| 5,550,318 A | 8/1996 | Adams et al. |
| 5,591,616 A | 1/1997 | Hiei et al. |
| 5,635,055 A | 6/1997 | Sweet et al. |
| 5,691,308 A | 11/1997 | Payne et al. |
| 5,710,020 A | 1/1998 | Adang |
| 5,750,871 A | 5/1998 | Moloney et al. |
| 5,824,877 A | 10/1998 | Hinchee et al. |
| 5,846,797 A | 12/1998 | Strickland |
| 5,981,840 A | 11/1999 | Zhao et al. |
| 6,083,499 A | 7/2000 | Narva et al. |
| 6,096,708 A | 8/2000 | Payne et al. |
| 6,114,138 A | 9/2000 | Adang |
| 6,127,180 A | 10/2000 | Narva et al. |
| 6,160,208 A | 12/2000 | Lundquist et al. |
| 6,166,302 A | 12/2000 | Merlo et al. |
| 6,251,656 B1 | 6/2001 | Adang |
| 6,340,593 B1 | 1/2002 | Cardineau et al. |
| 6,384,301 B1 | 5/2002 | Martinell et al. |
| 6,399,861 B1 | 6/2002 | Anderson et al. |
| 6,403,865 B1 | 6/2002 | Koziel et al. |
| 6,548,291 B1 | 4/2003 | Narva et al. |
| 6,573,240 B1 | 6/2003 | Payne et al. |
| 6,624,145 B1 | 9/2003 | Narva et al. |
| 6,624,344 B1 | 9/2003 | Rangan et al. |
| 6,699,984 B1 | 3/2004 | Ainley et al. |
| 7,060,876 B2 | 6/2006 | Hiei et al. |
| 7,179,902 B2 | 2/2007 | Cowen et al. |
| 7,838,733 B2 | 11/2010 | Wright et al. |
| 8,283,522 B2 | 10/2012 | Wright et al. |
| 2007/0130645 A1 | 6/2007 | Wu et al. |
| 2009/0093366 A1 | 4/2009 | Wright et al. |
| 2009/0104700 A1 | 4/2009 | Samuel et al. |
| 2011/0107455 A1 | 5/2011 | Lira et al. |
| 2011/0111442 A1* | 5/2011 | Shen ............... C12N 9/2437 435/18 |
| 2013/0157369 A1 | 6/2013 | Miller |

FOREIGN PATENT DOCUMENTS

| | | |
|---|---|---|
| WO | 9506722 A1 | 3/1995 |
| WO | 1997013402 A1 | 4/1997 |
| WO | 2005107437 A2 | 11/2005 |
| WO | 2011146524 A1 | 11/2011 |
| WO | 2012016222 A2 | 2/2012 |

(Continued)

OTHER PUBLICATIONS

Mitra et al. Structural and functional analyses of *Arabidopsis thaliana* chlorophyll a/b-binding protein (cab) promoters. Plant Molecular Biology. 1989. 12: 169-179.*
Sullivan et al. Isolation and characterization of a maize chlorophyll a/b binding protein gene that produces high levels of mRNA in the dark. Mol. Gen. Genet. 1989. 215: 431-440.*
Piechulla et al. Determination of steady-state mRNA levels of individual chlorophyll a/b binding protein genes of the tomato cab gene family. Mol. Gen. Genet. 1991. 230: 413-422.*
Whitelaw. 0G5EFO6TV ZM_0.7_1.5_KB *Zea mays* genomic clone ZMMBMa0845A12, genomic survey sequence. GenBank Accession No. CG442925. Published Sep. 17, 2003. pp. 1-2.*

(Continued)

*Primary Examiner* — Ashley K Buran

(74) *Attorney, Agent, or Firm* — Marcos P. Rivas; Barnes & Thornburg LLP

(57) ABSTRACT

Provided are vector constructs and methods for expressing a transgene in plant cells and/or plant tissues using gene regulatory elements, including the promoters, 5'-UTRs, introns, and/or 3'-UTRs, isolated from *Zea mays*.

9 Claims, 6 Drawing Sheets

(56) References Cited

FOREIGN PATENT DOCUMENTS

| WO | 2013016546 A2 | 1/2013 |
|---|---|---|
| WO | 2013116700 A1 | 8/2013 |

OTHER PUBLICATIONS

Gardiner et al. *Zea mays* PC0061381 mRNA sequence. GenBank Accession No. AY103750. Published May 13, 2008. pp. 1-2.*

International Search Report and Written Opinion issued in connection with International Application No. PCT/US2014/060620, dated Jan. 2, 2015, 12 pages.

Higgins et al., "Fast and sensitive multiple sequence alignments on a microcomputer", CABIOS Communications, vol. 5, No. 2, 1989, pp. 151-153.

Wilson, "NCBI GenBank Accession No. AC197488.3: *Zea mays* Chromosome 7 Clone CH201-27E13", submitted Sep. 23, 2013, 25 pages.

Storz, "An Expanding Universe of Noncoding RNAs", Science, vol. 296, May 17, 2002, pp. 1260-1263.

Needleman et al. "A General Method Applicable to the Search for Similarities in the Amino Acid Sequence of Two Proteins", J. Mol. Biol. (1970) 48, 443-453.

Pearson et al., "Improved tools for biological sequence comparison", Proc. Natl. Acad. Sci. USA vol. 85, pp. 2444-2448, Apr. 1998.

Higgins et al., "CLUSTAL: a package for performing multiple sequence alignment on a microcomputer", Gene, 73, (1988) 237-244.

Corpet, "Multiple sequence alignment with hierarchical clustering", Nucleic Acids Research, vol. 16, No. 22, 1988.

Huang et al., "Parallelization of a local similarity algorithm", Comp. Appl. Biosci. vol. 8, No. 2, pp. 155-165, 1992.

Smith et al., "Comparison of Biosequences", (1981) Adv. Appl. Math. 2:482-489.

Tatusova et al., "Blast 2 Sequences, a new tool for comparing protein and nucleotide sequences", FEMS Microbiology Letters 174 (1999) 247-250.

Chung et al., "Agrobacterium is not alone: gene transfer to plants by viruses and other bacteria", 2006 Trends Plant Sci 11(1): 1-4.

Rios et al., "Rapid identification of *Arabidopsis* insertion mutants by non-radioactive detection of T-DNA tagged genes", The Plant Journal (2002) 32, 243-253.

An et al., "Functional Analysis of the 3' Control Region of the Potato Wound-Inducible Proteinase Inhibitor II Gene", 1989 Plant Cell 1: 115-22.

Shagin et al., "GFP-like Proteins as Ubiquitous Metazoan Superfamily: Evolution of Functional Features and Structural Complexity", 2004 Mol. Biol. Evol. 21:841-50.

Vancanneyt et al., "Construction of an intron-containing marker gene: Splicing of the intron in transgenic plants and its use in monitoring early events in Agrobacterium-mediated plant transformation", 1990 Mol Gen Genet 220(2):245-250.

Stratagene "pBC Phagemids" Instruction Manual. Catalog #212215-#212218, revision A.01 pp. 1-23, retrieved from the internet on Aug. 9, 2017, http://www.chem-agilent.com/pdf/strata/212215.pdf.

Extended European Search Report, European Application No. 14854717.7-1401 / 3056075, dated May 10, 2017, 6 pages.

Database EMBL [Online] May 17, 2003, "PUHBR88TD ZM_0.6_1.0_KB *Zea mays* genomic clone ZMMBTa414P08, DNA sequence", XP002769452, retrieved from EBI accession No. EM_GSS:CC355941.

\* cited by examiner

SEQUENCE LISTING

<160> NUMBER OF SEQ ID NOS: 20

<210> SEQ ID NO 1
<211> LENGTH: 379
<212> TYPE: DNA
<213> ORGANISM: zea mays

<400> SEQUENCE: 1
ctggcgggcg ctcttcgccg ccggtgaggg cctcggcagt cggcacctgg cggtagccta    60

```
tccaaccgcg tcgcagacag agaggtatag agagagggaa agagcgctcg acgacttcgt    120
ttcacctacc tcacacaagt cctcttggtt cacagacggc cagagccact aactcagcca    180
gcgagctgta gctctcagtc tcagcgccgg ccacacattg agcaagcaac atgagtggag    240
aggagaccag tatcacatct tatccgatcc gatctacgtg gcagcttccc tgctctaacg    300
agacgacgcc acgtcagcag cgaagatcct gaacctatcc acgagtggcc gctgcaggcc    360
acaagctgcc ccggtggct                                                 379
```

<210> SEQ ID NO 2
<211> LENGTH: 119
<212> TYPE: DNA
<213> ORGANISM: Zea mays

<400> SEQUENCE: 2

```
ctgttcatcc aaatccgagt gttagaagtt actgttagta gccatcaaac agccaaatag     60
gttgaagaca gagtttggga actcggtttc acacagcggg caggaaagag agaatgcac    119
```

<210> SEQ ID NO 3
<211> LENGTH: 91
<212> TYPE: DNA
<213> ORGANISM: Zea mays

<400> SEQUENCE: 3

```
gtaggtatat gtatacatgt gaagtctgat gagtacgtac gtgaggaaaa gaccgacgag     60
atcactgacg acggcatatg cacgcacgca g                                    91
```

<210> SEQ ID NO 4
<211> LENGTH: 152
<212> TYPE: DNA
<213> ORGANISM: zea mays

<400> SEQUENCE: 4

```
cccatcccac gcctcgccgt gtccaggctt taagccacac gcacttgagc tccaccgcca     60
ctaccaccag taccacacca ctccgcgcta gctgaggacg gtacagcggc acagaggtgc    120
gacgtacgac gacgacgacg caggcgccac ac                                  152
```

<210> SEQ ID NO 5
<211> LENGTH: 658
<212> TYPE: DNA
<213> ORGANISM: Zea mays

<400> SEQUENCE: 5

```
tgctgggact gttcatccaa atccgagtgt tagaagttac tgttagtagc catcaaacag     60
ccaaataggt tgaagacaga gtttgggaac tcggtttcac acagcgggca ggaaagagag    120
aatgcacctg gcgggcgctc ttcgccgccg gtgagggcct cggcagtcgg cacctggcgg    180
tagcctatcc aaccgcgtcg cagacagaga ggtatagaga gagggaaaga gcgctcgacg    240
acttcgtttc acctacctca cacaagtcct cttggttcac agacggccag agccactaac    300
tcagccagcg agctgtagct ctcagtctca gcgccggcca cattgagc aagcaacatg    360 agtggagagg agaccagtat cacatcttat ccgatccgat ctacgtggca gcttccctgc    420
tctaacgaga cgacgccacg tcagcagcga agatcctgaa cctatccacg agtggccgct    480
gcaggccaca agctgccccg gtggctccca tccacgcct cgccgtgtcc aggctttaag    540
ccacacgcac ttgagctcca ccgccactac caccagtacc acaccactcc gcgctagctg    600
```

```
aggacggtac agcggcacag aggtgcgacg tacgacgacg acgacgcagg cgccacac    658
```

<210> SEQ ID NO 6
<211> LENGTH: 295
<212> TYPE: DNA
<213> ORGANISM: Zea mays

<400> SEQUENCE: 6

```
atccctacgt cgccgttgtt aagatcagac tcagcagcct cgatcgcgcc gccggccggc    60
aggtgcaggt ggtgactttg taacgtgtgt gcgtgcgtac gtgtacattg catccatctt   120
ggttccaatg dacatatagc tcctgttgct cctctagtcc tcttgcgttg accccgatcg   180
atgagtatga cttctacctt ccatgatagc aattagcaag cggttaaaac ttataaaaaa   240
gagataaatc cagatcatat ctgaaagaaa gaataataaa tatcactaac tagtg         295
```

<210> SEQ ID NO 7
<211> LENGTH: 1449
<212> TYPE: DNA
<213> ORGANISM: Zea mays

<400> SEQUENCE: 7

```
tgctgggact gttcatccaa atccgagtgt tagaagttac tgttagtagc catcaaacag    60
ccaaataggt tgaagacaga gtttgggaac tcggtttcac acagcgggca ggaaagagag   120
aatgcacctg gcgggcgctc ttcgccgccg gtgagggcct cggcagtcgg cacctggcgg   180
tagcctatcc aaccgcgtcg cagacagaga ggtatagaga gagggaaaga gcgctcgacg   240
acttcgtttc acctacctca cacaagtcct cttggttcac agacggccag agccactaac   300
tcagccagcg agctgtagct ctcagtctca gcgccggcca cacattgagc aagcaacatg   360
agtggagagg agaccagtat cacatcttat ccgatccgat ctacgtggca gcttccctgc   420
tctaacgaga cgacgccacg tcagcagcga agatcctgaa cctatccacg agtggccgct   480
gcaggccaca agctgccccg gtggctccca tcccacgcct cgccgtgtcc aggctttaag   540
ccacacgcac ttgagctcca ccgccactac caccagtacc acaccactcc gcgctagctg   600
aggacggtac agcggcacag aggtgcgacg tacgacgacg acgacgcagg cgccacacat   660
ggcatcccag ctctccgccg ccgtgccccg gttccacggc ctccggggct acgccgcgcc   720
caggtccgcg gtggcagcgc tgccgtccgt gagggtgggc aggaagaggt cgtcgtcgca   780
gggcatccgc tgcgactaca tcggctccgc caccaacctg gtaggtatat gtatacatgt   840
gaagtctgat gagtacgtac gtgaggaaaa gaccgacgag atcactgacg acggcatatg   900
cacgcacgca gatcatggtg acgacgacga cgctgatgct gttcgcgggg cggttcgggc   960
tggcgccgtc cgcgaaccgc aaggcgacgg cggggctgaa gctggaggcg cgcgactccg  1020
gcctgcagac gggtgacccc gccgggttca ccctcgccga cacgctggcc tgcggcgccg  1080
tcggccacat cctcggcgtc ggcatcgtgc tcgggctcaa gaacaccggc gcctcgacc   1140
agatcatcgg ctagatccct acgtcgccgt tgttaagatc agactcagca gcctcgatcg  1200
cgccgccggc cggcaggtgc aggtggtgac tttgtaacgt gtgtgcgtgc gtacgtgtac  1260
attgcatcca tcttggttcc aatgacacata tagctcctgt tgctcctcta gtcctcttgc  1320
gttgaccccg atcgatgagt atgacttcta ccttccatga tagcaattag caagcggtta  1380
aaacttataa aaagagata atccagatc atatctgaaa gaaagaataa taatatcac   1440
taactagtg                                                           1449
```

```
<210> SEQ ID NO 8
<211> LENGTH: 17
<212> TYPE: DNA
<213> ORGANISM: artificial sequence
<220> FEATURE:
<223> OTHER INFORMATION: Forward Primer: TQ.8v6.1.F

<400> SEQUENCE: 8
gccataccct ccagttg                                                   17

<210> SEQ ID NO 9
<211> LENGTH: 23
<212> TYPE: DNA
<213> ORGANISM: artificial sequence
<220> FEATURE:
<223> OTHER INFORMATION: Reverse Primer: TQ.8v6.1.R

<400> SEQUENCE: 9
gccgttgatg gagtagtaga tgg                                            23

<210> SEQ ID NO 10
<211> LENGTH: 18
<212> TYPE: DNA
<213> ORGANISM: artificial sequence
<220> FEATURE:
<223> OTHER INFORMATION: Probe: TQ.8v6.1.MGB.P

<400> SEQUENCE: 10
ccgaatccaa cggcttca                                                  18

<210> SEQ ID NO 11
<211> LENGTH: 18
<212> TYPE: DNA
<213> ORGANISM: artificial sequence
<220> FEATURE:
<223> OTHER INFORMATION: Forward Primer: InvertaseF

<400> SEQUENCE: 11
tggcggacga cgacttgt                                                  18

<210> SEQ ID NO 12
<211> LENGTH: 19
<212> TYPE: DNA
<213> ORGANISM: artificial sequence
<220> FEATURE:
<223> OTHER INFORMATION: Reverse Primer: InvertaseR

<400> SEQUENCE: 12
aaagtttgga ggctgccgt                                                 19

<210> SEQ ID NO 13
<211> LENGTH: 21
<212> TYPE: DNA
<213> ORGANISM: artificial sequence
<220> FEATURE:
<223> OTHER INFORMATION: InvertaseProbe

<400> SEQUENCE: 13
cgagcagacc gccgtgtact t                                              21

<210> SEQ ID NO 14
<211> LENGTH: 20
<212> TYPE: DNA
<213> ORGANISM: artificial sequence
<220> FEATURE:
<223> OTHER INFORMATION: AAD1 Forward Primer
```

```
<400> SEQUENCE: 14
tgttcggttc cctctaccaa                                                20

<210> SEQ ID NO 15
<211> LENGTH: 22
<212> TYPE: DNA
<213> ORGANISM: artificial sequence
<220> FEATURE:
<223> OTHER INFORMATION: AAD1 Reverse Primer

<400> SEQUENCE: 15
caacatccat caccttgact ga                                             22

<210> SEQ ID NO 16
<211> LENGTH: 24
<212> TYPE: DNA
<213> ORGANISM: artificial sequence
<220> FEATURE:
<223> OTHER INFORMATION: AAD1 Probe

<400> SEQUENCE: 16
cacagaaccg tcgcttcagc aaca                                           24

<210> SEQ ID NO 17
<211> LENGTH: 21
<212> TYPE: DNA
<213> ORGANISM: artificial sequence
<220> FEATURE:
<223> OTHER INFORMATION: PhiYFP v3  Forward Primer

<400> SEQUENCE: 17
cgtgttggga agaacttgg a                                               21

<210> SEQ ID NO 18
<211> LENGTH: 18
<212> TYPE: DNA
<213> ORGANISM: artificial sequence
<220> FEATURE:
<223> OTHER INFORMATION: PhiYFP v3  Reverse Primer

<400> SEQUENCE: 18
ccgtggttgg cttggtct                                                  18

<210> SEQ ID NO 19
<211> LENGTH: 15
<212> TYPE: DNA
<213> ORGANISM: artificial sequence
<220> FEATURE:
<223> OTHER INFORMATION: PhiYFP v3  Probe

<400> SEQUENCE: 19
cactccccac tgcct                                                     15

<210> SEQ ID NO 20
<211> LENGTH: 496
<212> TYPE: DNA
<213> ORGANISM: zea mays

<400> SEQUENCE: 20
atggcatccc agctctccgc cgccgtgccc cggttccacg gcctcggggg ctacgccgcg    60
cccaggtccg cggtggcagc gctgccgtcc gtgagggtgg gcaggaagag gtcgtcgtcg   120
cagggcatcc gctgcgacta catcggctcc gccaccaacc tggtaggtat atgtatacat   180
gtgaagtctg atgagtacgt acgtgaggaa aagaccgacg agatcactga cgacggcata   240
```

-continued

```
tgcacgcacg cagatcatgg tgacgacgac gacgctgatg ctgttcgcgg ggcggttcgg    300
gctggcgccg tccgcgaacc gcaaggcgac ggcggggctg aagctggagg cgcgcgactc    360
cggcctgcag acgggtgacc ccgccggggtt caccctcgcc gacacgctgg cctgcggcgc    420
cgtcggccac atcctcggcg tcggcatcgt gctcgggctc aagaacaccg gcgccctcga    480
ccagatcatc ggctag                                                    496
```

ZEA MAYS REGULATORY ELEMENTS AND USES THEREOF

CROSS-REFERENCE TO RELATED APPLICATIONS

This application claims the benefit, under 35 U.S.C. 5 § 119(e), to U.S. Provisional Patent Application No. 61/890,904, filed Oct. 15, 2013, the contents of which are incorporated by reference in their entirety into the present application.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: One 8 KB ASCII (Text) file named "74276" created on Oct. 3, 2014.

FIELD OF THE INVENTION

This invention is generally related to the field of plant molecular biology, and more specifically, to the field of stable expression of genes in transgenic plants.

BACKGROUND

Plant transformation is an attractive technology for use in introducing agronomically desirable traits or characteristics into different crop plant species. Plant species are developed and/or modified to have particular desirable traits. Generally, desirable traits include, for example, improving nutritional value quality, increasing yield, conferring pest or insect resistance, disease resistance, increasing drought and stress tolerance, improving horticultural qualities (e.g., pigmentation and growth), imparting herbicide tolerance, enabling the production of industrially useful compounds and/or materials from the plant, and/or enabling the production of pharmaceuticals.

Transgenic plants comprising multiple transgenes stacked at a single genomic locus are produced via plant transformation technologies. Plant transformation technologies confer the introduction of transgenes into a plant cell, recovery of a fertile transgenic plant that contains the stably integrated copy of the transgene in the plant genome, and subsequent transgene expression via transcription and translation of the transgene(s). Thereby resulting in transgenic plants that possess desirable traits and phenotypes. Each transgene in a stack typically requires an independent promoter for gene expression within a plant, and thus multiple promoters are used in a transgene stack.

The need for co-expression of multiple transgenes for regulating the same trait frequently results in the repeated use of the same promoter to drive expression of the multiple transgenes. However, the repeated use of promoters comprising sequences that share a high level of sequence identity may lead to homology-based gene silencing (HBGS). HBGS has been observed to occur frequently in transgenic plants (Peremarti et al., 2010) when repetitive DNA sequences are used within a transgene. In addition, repeated use of similar DNA sequences in transgene constructs has proven to be challenging in *Agrobacterium* due to recombination and instability of the plasmid.

Described herein are maize gene regulatory elements (e.g., promoter, 5'-UTR, and 3'-UTR). Further described are constructs and methods utilizing maize regulatory elements.

SUMMARY

Disclosed herein are purified polynucleotides, vectors, constructs and methods for expressing a transgene in plant cells and/or plant tissues. In one embodiment, regulatory elements of a chlorophyll a/b gene are purified from the *Zea mays* genomes and recombined with sequences not natively linked to said regulatory elements to create an expression vector for expressing transgenes in plant cells not native to the chlorophyll a/b regulatory sequences. In one embodiment an expression vector is provided wherein the regulatory elements of a chlorophyll a/b gene are operably linked to a polylinker sequence. Such an expression vector eases the insertion of a gene, transgene, or gene cassette into the vector in an operably linked state with the chlorophyll a/b gene regulatory sequences.

In an embodiment, a construct is provided comprising a *Zea mays* chlorophyll a/b promoter of SEQ ID NO:1. In an embodiment, a gene expression cassette is provided comprising a *Zea mays* chlorophyll a/b promoter operably linked to a transgene. In an embodiment, a gene expression cassette includes a *Zea mays* chlorophyll a/b 5'-UTR operably linked to a transgene. In an embodiment, a gene expression cassette includes a *Zea mays* chlorophyll a/b 5'-UTR operably linked to a promoter. In an embodiment, a gene expression cassette includes a *Zea mays* chlorophyll a/b intron operably linked to a transgene. In an embodiment, a gene expression cassette includes a *Zea mays* chlorophyll a/b intron operably linked to a promoter. In an embodiment, a construct includes a gene expression cassette *Zea mays* chlorophyll a/b 3'-UTR. In an embodiment, a gene expression cassette includes *Zea mays* chlorophyll a/b 3'-UTR operably linked to a transgene. In an embodiment, a gene expression cassette includes at least one, two, three, five, six, seven, eight, nine, ten, or more transgenes.

In an embodiment, a gene expression cassette includes independently a) a *Zea mays* chlorophyll a/b promoter, b) a *Zea mays* chlorophyll a/b intron, c) a *Zea mays* chlorophyll a/b 5'-UTR, and d) a *Zea mays* chlorophyll a/b 3'-UTR.

In accordance with one embodiment a nucleic acid vector is provided comprising a promoter operably linked to a non-chlorophyll a/b transgene, wherein the promoter consists of SEQ ID NO:1 or a sequence having 90% sequence identity with SEQ ID NO:1. In a further embodiment the nucleic acid vector comprises a gene cassette, wherein the gene cassette comprises a promoter, a non-chlorophyll a/b transgene and a 3' untranslated region, wherein the promoter consists of SEQ ID NO:1 operably linked to a first end of a transgene, wherein the second end of the transgene is operably linked to a 3' untranslated sequence consisting of SEQ ID NO:6.

Methods of growing plants expressing a transgene using the *Zea mays* chlorophyll a/b promoters, 5'-UTRs, introns, and 3'-UTRs are disclosed herein. Methods of culturing plant tissues and cells expressing a transgene using the *Zea mays* chlorophyll a/b promoters, 5'-UTRs, introns, and 3'-UTRs are also disclosed herein. In an embodiment, methods as disclosed herein include tissue-specific gene expression in plant stem, leaf, cob, silk, kernel, stem, husk and pollen tissues.

In a further embodiment, a method of enhancing the over-expression of a gene of interest contained within a second gene expression cassette is disclosed herein.

In accordance with one embodiment a plant, plant tissue, or plant cell is provided comprising a promoter operably linked to a non-chlorophyll a/b transgene, wherein the promoter comprises SEQ ID NO:1 or SEQ ID NO:5. In accordance with one embodiment a plant or plant cell is provided comprising SEQ ID NO:1 or SEQ ID NO:5, or a sequence that has 90% sequence identity with SEQ ID NO:1 operably linked to a transgene. In one embodiment the plant is a corn variety. In one embodiment a plant, plant tissue, or plant cell is provided comprising a promoter operably linked to a non-chlorophyll a/b transgene, wherein the promoter consists of SEQ ID NO:1 or SEQ ID NO:5. In one embodiment a plant or plant cell is provided comprising a gene cassette, wherein the gene cassette comprises a promoter operably linked to a transgene, further wherein the promoter consists SEQ ID NO:1 or SEQ ID NO:5. In a further embodiment the promoter is operably linked to a first end of a transgene, wherein the second end of the transgene is operably linked to a 3' untranslated sequence consisting of SEQ ID NO:6.

DETAILED DESCRIPTION

Definitions

Figure 1:
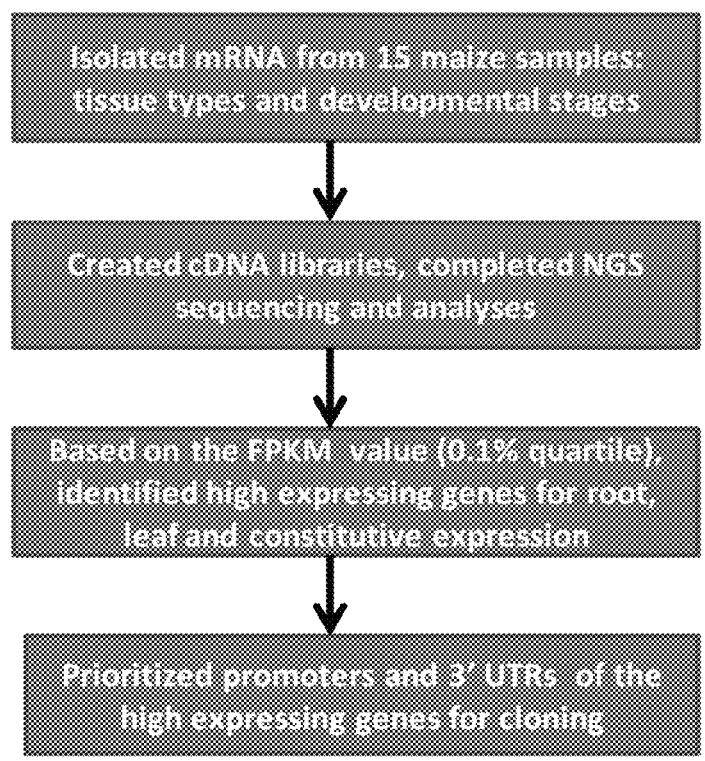
FIG. 1 is a schematic flow chart displaying the process of identifying high expressing genes in maize using a transcriptional profiling approach with Next Generation Sequencing (NGS).
Figure 2:
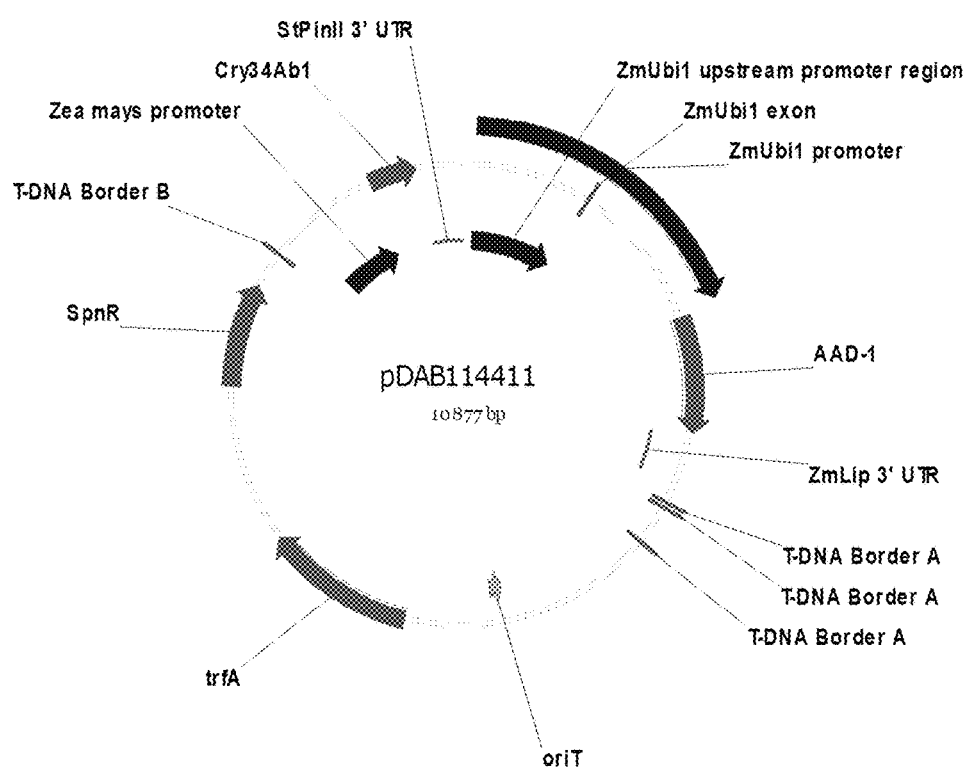
FIG. 2 shows the pDAB114411 vector plasmid map depicting a gene expression cassette for expression of a cry34Ab1 reporter gene driven by the Zea mays promoter of SEQ ID NO:1 and terminated by the StPinII 3' UTR regulatory element.
Figure 3:
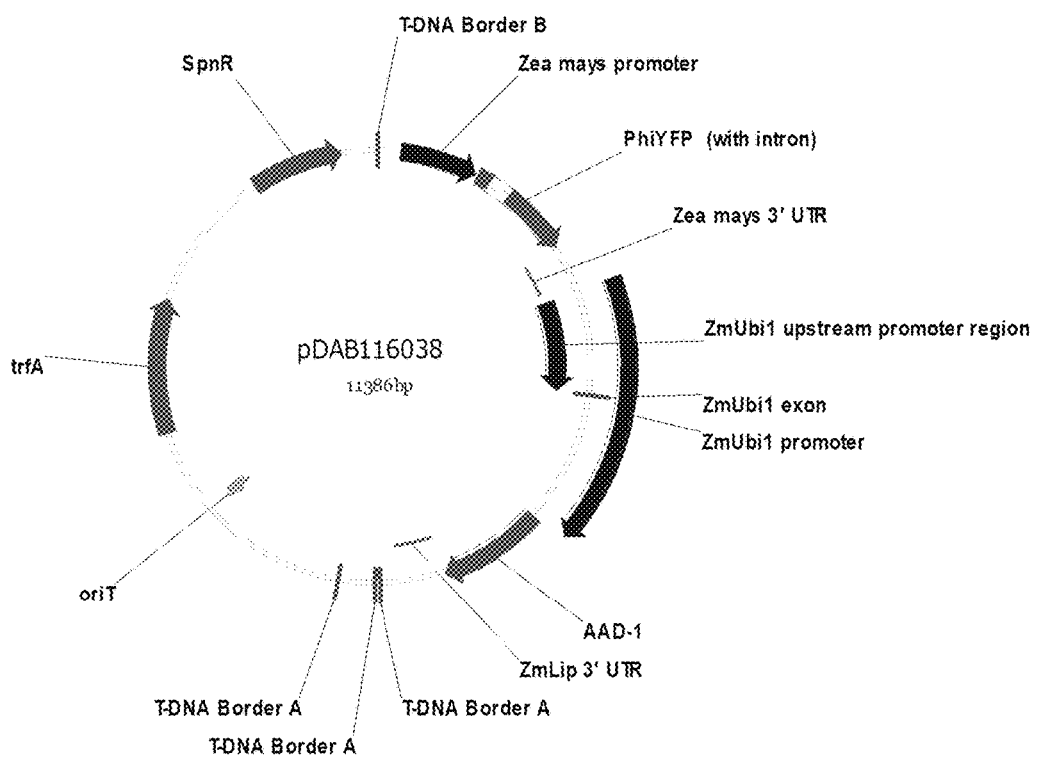
FIG. 3 shows the pDAB116038 vector plasmid map depicting a gene expression cassette for expression of a phiYFP reporter gene driven by the Zea mays promoter of SEQ ID NO:1 and terminated by the Zea mays 3'-UTR of SEQ ID NO:4 regulatory elements.
Figure 4:
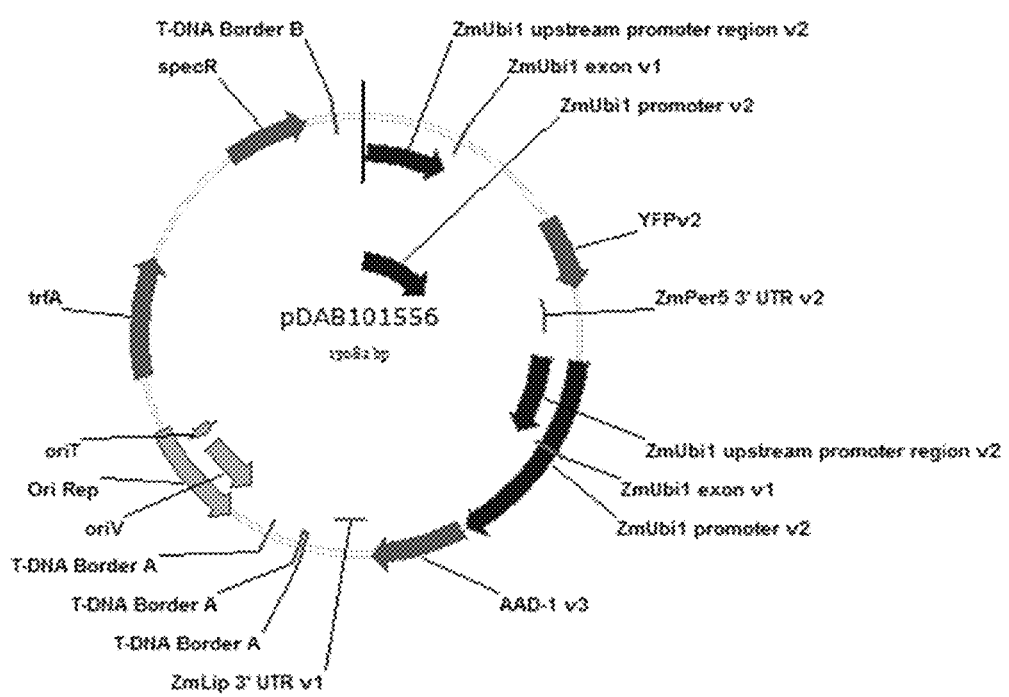
FIG. 4 shows a vector plasmid map of the pDAB101556 control vector containing a YFP reporter gene instead of the cry34Ab1 reporter gene present in the test promoter construct, pDAB114411. The YFP gene expression was driven by the Zea mays ubiquitin-1 (ZmUbi1) promoter and terminated by the Zea mays Per5 (ZmPer5) 3'-UTR.
Figure 5:
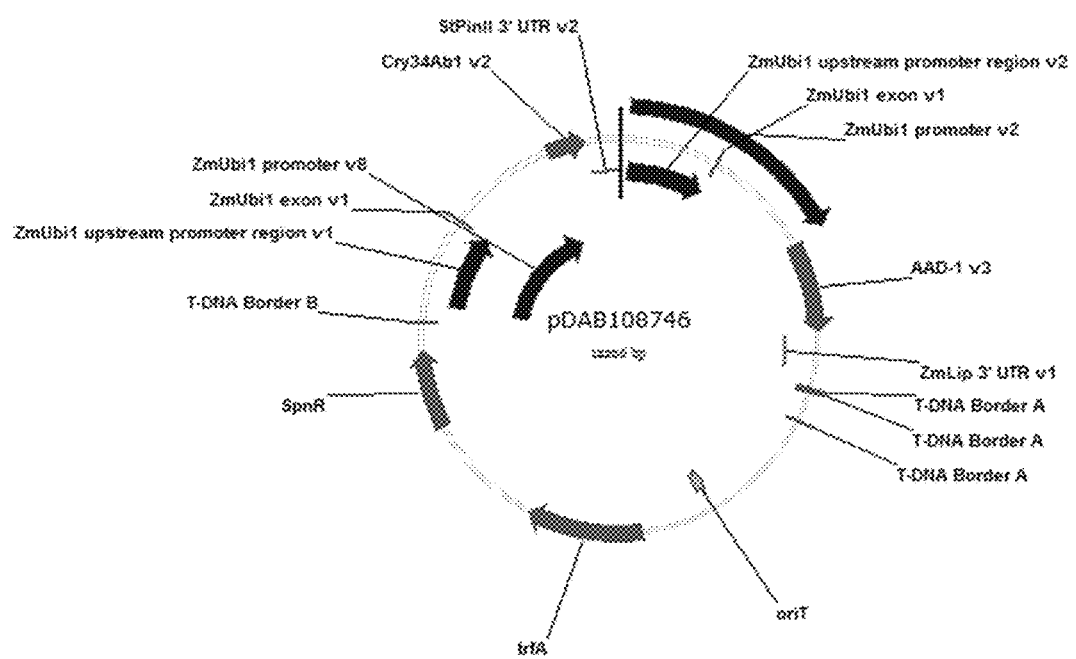
FIG. 5 shows a vector plasmid map of pDAB108746, a positive control vector containing the cry34Ab1 reporter gene driven by the ZmUbi1 promoter and terminated by the StPinII 3'-UTR.
Figure 6:
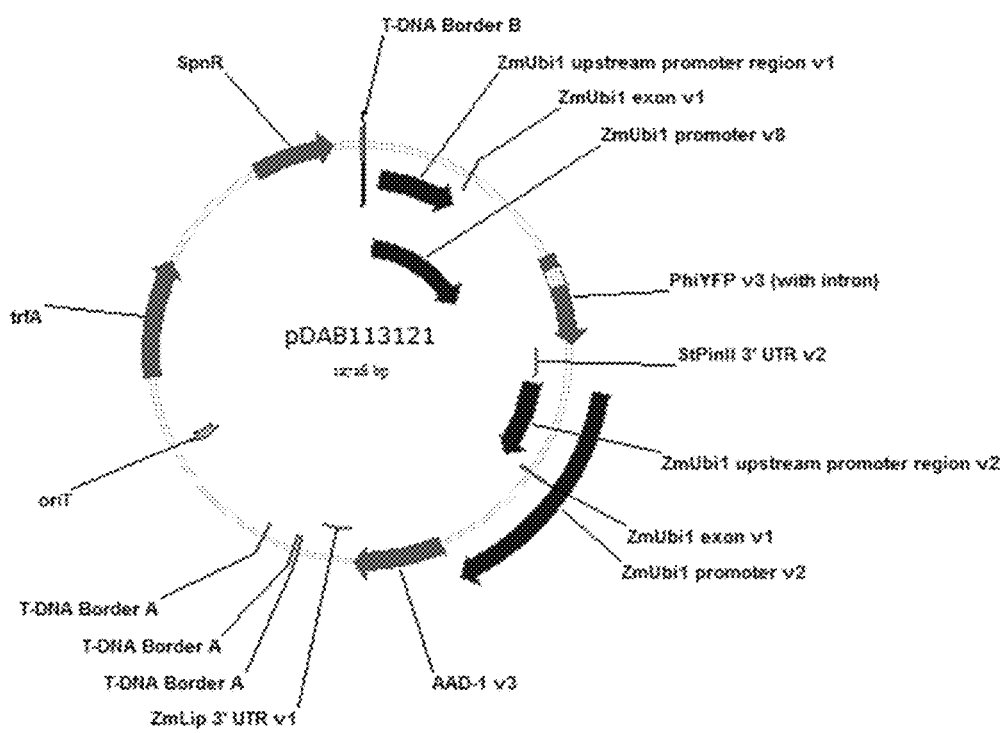
FIG. 6 shows a map of pDAB113121, a positive control vector. This plasmid contains a phiYFP reporter gene driven by the ZmUbi1 promoter and terminated by the StPinII 3' UTR. The phiYFP gene contains an intron. The aad-1 gene cassette is identical in both pDAB113121 and pDAB116038.

In describing and claiming the invention, the following terminology will be used in accordance with the definitions set forth below.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "backcrossing" refers to a process in which a breeder crosses hybrid progeny back to one of the parents, for example, a first generation hybrid F1 with one of the parental genotypes of the F1 hybrid.

A "promoter" is a DNA regulatory region capable of binding RNA polymerase in a cell and initiating transcription of a downstream (3' direction) coding sequence. A promoter may contain specific sequences that are recognized by transcription factors. These factors may bind to a promoter DNA sequence, which results in the recruitment of RNA polymerase. For purposes of defining the present invention, the promoter sequence is bound at its 3' terminus by the transcription initiation site (i.e., ribosome binding site) and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. The promoter may be operatively associated with other expression control sequences, including enhancer and repressor sequences.

For the purposes of the present disclosure, a "gene", includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

As used herein a "transgene" is defined to be a nucleic acid sequence that encodes a gene product, including for example, but not limited to, an mRNA. In one embodiment the transgene is an exogenous nucleic acid, where the transgene sequence has been introduced into a host cell by genetic engineering (or the progeny thereof) where the transgene is not normally found. In one example, a transgene encodes an industrially or pharmaceutically useful compound, or a gene encoding a desirable agricultural trait (e.g., an herbicide-resistance gene). In yet another example, a transgene is an antisense nucleic acid sequence, wherein expression of the antisense nucleic acid sequence inhibits expression of a target nucleic acid sequence. In one embodiment the transgene is an endogenous nucleic acid, wherein additional genomic copies of the endogenous nucleic acid are desired, or a nucleic acid that is in the antisense orientation with respect to the sequence of a target nucleic acid in a host organism.

As used herein the term "non-chlorophyll a/b transgene" is any transgene that encodes a protein with less than 90% sequence identity to the protein encoded by the Zea may chlorophyll a/b coding sequence (SEQ ID NO:20).

"Gene expression" as defined herein is the conversion of the information, contained in a gene, into a gene product.

A "gene product" as defined herein is any product produced by the gene. For example the gene product can be the direct transcriptional product of a gene (e.g., mRNA, tRNA, rRNA, small RNA, antisense RNA, interfering RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation. Gene expression can be influenced by external signals, for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, ELISA assay, or in vitro, in situ, or in vivo protein activity assay(s).

As used herein, the term "small RNA" refers to several classes of non-coding ribonucleic acid (ncRNA). The term small RNA describes the short chains of ncRNA produced in bacterial cells, animals, plants, and fungi. These short chains of ncRNA may be produced naturally within the cell or may be produced by the introduction of an exogenous sequence that expresses the short chain or ncRNA. The small RNA sequences do not directly code for a protein, and differ in function from other RNA in that small RNA sequences are only transcribed and not translated. The small RNA sequences are involved in other cellular functions, including gene expression and modification. Small RNA molecules are usually made up of about 20 to 30 nucleotides. The small RNA sequences may be derived from longer precursors. The precursors form structures that fold back on each other in self-complementary regions; they are then processed by the nuclease Dicer in animals, DCL1 in plants, or other enzymes that process the small RNA molecule.

Many types of small RNA exist either naturally or produced artificially, including microRNAs (miRNAs), short interfering RNAs (siRNAs), antisense RNA, short hairpin RNA (shRNA), and small nucleolar RNAs (snoRNAs). Certain types of small RNA, such as microRNA and siRNA, are important in gene silencing and RNA interference (RNAi). Gene silencing is a process of genetic regulation in which a gene that would normally be expressed is "turned off" by an intracellular element, in this case, the small RNA. The protein that would normally be formed by this genetic information is not formed due to interference, and the information coded in the gene is blocked from expression.

As used herein, the term "small RNA" encompasses RNA molecules described in the literature as "tiny RNA" (Storz, (2002) *Science* 296:1260-3; Illangasekare et al., (1999) *RNA* 5:1482-1489); prokaryotic "small RNA" (sRNA) (Wassarman et al., (1999) *Trends Microbiol.* 7:37-45); eukaryotic "noncoding RNA (ncRNA)"; "micro-RNA (miRNA)"; "small non-mRNA (snmRNA)"; "functional RNA (fRNA)"; "transfer RNA (tRNA)"; "catalytic RNA" [e.g., ribozymes, including self-acylating ribozymes (Illangaskare et al., (1999) *RNA* 5:1482-1489); "small nucleolar RNAs (snoRNAs)"; "tmRNA" (a.k.a. "10S RNA", Muto et al., (1998) *Trends Biochem Sci.* 23:25-29; and Gillet et al., (2001) *Mol Microbiol.* 42:879-885); RNAi molecules including without limitation "small interfering RNA (siRNA)", "endoribonuclease-prepared siRNA (e-siRNA)", "short hairpin RNA (shRNA)", and "small temporally regulated RNA (stRNA)"; "diced siRNA (d-siRNA)", and aptamers, oligonucleotides and other synthetic nucleic acids that comprise at least one uracil base.

As used herein, the term "intron" is defined as any nucleic acid sequence comprised in a gene (or expressed nucleotide sequence of interest) that is transcribed but not translated. Introns include untranslated nucleic acid sequence within an expressed sequence of DNA, as well as corresponding sequence in RNA molecules transcribed therefrom. A construct described herein can also contain sequences that enhance translation and/or mRNA stability such as introns. An example of one such intron is the first intron of gene II of the histone H3 variant of *Arabidopsis thaliana* or any other commonly known intron sequence. Introns can be used in combination with a promoter sequence to enhance translation and/or mRNA stability.

As used herein, the terms "5' untranslated region" or "5'-UTR" is defined as the untranslated segment in the 5' terminus of pre-mRNAs or mature mRNAs. For example, on mature mRNAs, a 5'-UTR typically harbors on its 5' end a 7-methylguanosine cap and is involved in many processes such as splicing, polyadenylation, mRNA export towards the cytoplasm, identification of the 5' end of the mRNA by the translational machinery, and protection of the mRNAs against degradation.

As used herein, the terms "transcription terminator" is defined as the transcribed segment in the 3' terminus of pre-mRNAs or mature mRNAs. For example, longer stretches of DNA beyond "polyadenylation signal" site is transcribed as a pre-mRNA. This DNA sequence usually contains one or more transcription termination signals for the proper processing of the pre-mRNA into mature mRNA.

As used herein, the term "3' untranslated region" or "3'-UTR" is defined as the untranslated segment in a 3' terminus of the pre-mRNAs or mature mRNAs. For example, on mature mRNAs this region harbors the poly-(A) tail and is known to have many roles in mRNA stability, translation initiation, and mRNA export.

As used herein, the term "polyadenylation signal" designates a nucleic acid sequence present in mRNA transcripts that allows for transcripts, when in the presence of a poly-(A) polymerase, to be polyadenylated on the polyadenylation site, for example, located 10 to 30 bases downstream of the poly-(A) signal. Many polyadenylation signals are known in the art and are useful for the present invention. An exemplary sequence includes AAUAAA and variants thereof, as described in Loke J., et al., (2005) Plant Physiology 138(3); 1457-1468.

The term "isolated" as used herein means having been removed from its natural environment, or removed from other compounds present when the compound is first formed. The term "isolated" embraces materials isolated from natural sources as well as materials (e.g., nucleic acids and proteins) recovered after preparation by recombinant expression in a host cell, or chemically-synthesized compounds such as nucleic acid molecules, proteins, and peptides.

The term "purified", as used herein relates to a molecule or compound in a form that is substantially free of contaminants normally associated with the molecule or compound in a native or natural environment, or substantially enriched in concentration relative to other compounds present when the compound is first formed, and means having been increased in purity as a result of being separated from other components of the original composition. The term "purified nucleic acid" is used herein to describe a nucleic acid sequence which has been separated, produced apart from, or purified away from other biological compounds including, but not limited to polypeptides, lipids and carbohydrates, while effecting a chemical or functional change in the component (e.g., a nucleic acid may be purified from a chromosome by removing protein contaminants and breaking chemical bonds connecting the nucleic acid to the remaining DNA in the chromosome).

As used herein, the terms "Homology-Based Gene Silencing" or "HBGS" are generic terms that include both transcriptional gene silencing and posttranscriptional gene silencing. Silencing of a target locus by an unlinked silencing locus can result from transcription inhibition (Transcriptional Gene Silencing; TGS) or mRNA degradation (Post-Transcriptional Gene Silencing; PTGS), owing to the production of double-stranded RNA (dsRNA) corresponding to promoter or transcribed sequences, respectively. Involvement of distinct cellular components in each process suggests that dsRNA-induced TGS and PTGS likely results from the diversification of an ancient common mechanism. However, a strict comparison of TGS and PTGS has been difficult to achieve because it generally relies on the analysis of distinct silencing loci. A single transgene locus can be described to trigger both TGS and PTGS, owing to the production of dsRNA corresponding to promoter and transcribed sequences of different target genes.

As used herein, the terms "nucleic acid molecule", "nucleic acid", or "polynucleotide" (all three terms are synonymous with one another) refer to a polymeric form of nucleotides, which may include both sense and anti-sense strands of RNA, cDNA, genomic DNA, and synthetic forms, and mixed polymers thereof. "A nucleotide" may refer to a ribonucleotide, deoxyribonucleotide, or a modified form of either type of nucleotide. A nucleic acid molecule is usually at least 10 bases in length, unless otherwise specified. The terms may refer to a molecule of RNA or DNA of indeterminate length. The terms include single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" relative to a further element if they are bonded or would be bonded to the same nucleic acid in the 5' direction from that element. Similarly, discrete elements may be "downstream" relative to a further element if they are or would be bonded to the same nucleic acid in the 3' direction from that element.

As used herein, the term "base position", refers to the location of a given base or nucleotide residue within a designated nucleic acid. A designated nucleic acid may be defined by alignment with a reference nucleic acid.

As used herein, the term "hybridization" refers to a process where oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and bonding of a pyrimidine to a purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

As used herein, the terms "specifically hybridizable" and "specifically complementary" refers to a sufficient degree of complementarity such that stable and specific binding occurs between an oligonucleotide and the DNA or RNA target. Oligonucleotides need not be 100% complementary to its target sequence to specifically hybridize. An oligonucleotide is specifically hybridizable when binding of the oligonucleotide to the target DNA or RNA molecule interferes with the normal function of the target DNA or RNA, and there is sufficient degree of complementarity to avoid non-specific binding of an oligonucleotide to non-target sequences under conditions where specific binding is desired, for example under physiological conditions in the case of in vivo assays or systems. Such binding is referred to as specific hybridization. Hybridization conditions resulting in particular degrees of stringency will vary depending upon the nature of the chosen hybridization method and the composition and length of the hybridizing nucleic acid sequences. Generally, the temperature of hybridization and the ionic strength (especially $Na^+$ and/or $Mg^{2+}$ concentration) of a hybridization buffer will contribute to the stringency of hybridization, though wash times also influence stringency. Calculations regarding hybridization conditions required for attaining particular degrees of stringency are discussed in Sambrook et al. (ed.), Molecular Cloning: A Laboratory Manual, 2nd ed., vol. 1-3, Cold Spring Harbor Laboratory Press, Cold Spring Harbor, N.Y., 1989, chs. 9 and 11.

As used herein, the term "stringent conditions" encompasses conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize. In particular embodiments, stringent conditions can include hybridization at 65° C., followed by washes at 65° C. with 0.1×SSC/0.1% SDS for 40 minutes. The following are representative, non-limiting hybridization conditions:

Very High Stringency: hybridization in 5×SSC buffer at 65° C. for 16 hours; wash twice in 2×SSC buffer at room temperature for 15 minutes each; and wash twice in 0.5×SSC buffer at 65° C. for 20 minutes each.

High Stringency: Hybridization in 5-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency: Hybridization in 6×SSC buffer at room temperature to 55° C. for 16-20 hours; wash at least twice in 2×-3×SSC buffer at room temperature to 55° C. for 20-30 minutes each.

In an embodiment, specifically hybridizable nucleic acid molecules can remain bound under very high stringency hybridization conditions. In an embodiment, specifically hybridizable nucleic acid molecules can remain bound under high stringency hybridization conditions. In an embodiment, specifically hybridizable nucleic acid molecules can remain bound under moderate stringency hybridization conditions.

As used herein, the term "oligonucleotide" refers to a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, an oligonucleotide is typically referred to as a "primer", which allows a DNA polymerase to extend the oligonucleotide and replicate the complementary strand.

As used herein, the terms "Polymerase Chain Reaction" or "PCR" refer to a procedure or technique in which minute amounts of nucleic acid, RNA and/or DNA, are amplified as described in U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51:263 (1987); Erlich, ed., PCR Technology, (Stockton Press, NY, 1989).

As used herein, the term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

As used herein, the term "probe" refers to an oligonucleotide that hybridizes to a target sequence. In the TaqMan® or TaqMan®-style assay procedure, the probe hybridizes to a portion of the target situated between the annealing site of the two primers. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides. A probe can further include a detectable label, e.g., a fluorophore (Texas-Red®, Fluorescein isothiocyanate, etc.,). The detectable label can be covalently attached directly to the probe oligonucleotide, e.g., located at the probe's 5' end or at the probe's 3' end. A probe including a fluorophore may also further include a quencher, e.g., Black Hole Quencher™, Iowa Black™, etc.

As used herein, the terms "sequence identity" or "identity" can be used interchangeably and refer to nucleic acid residues or amino acid sequences in two sequences that are the same when aligned for maximum correspondence over a specified comparison window.

As used herein, the term "percentage of sequence identity" refers to a value determined by comparing two optimally aligned sequences (e.g., nucleic acid sequences or amino acid sequences) over a comparison window, wherein the portion of a sequence in the comparison window may comprise additions or deletions (i.e., gaps) as compared to a reference sequence (which does not comprise additions or deletions) for optimal alignment of the two sequences. A percentage is calculated by determining the number of positions at which an identical nucleic acid or amino acid residue occurs in both sequences to yield the number of matched positions, dividing the number of matched positions by the total number of positions in the comparison window, and multiplying the result by 100 to yield the percentage of sequence identity. Methods for aligning sequences for comparison are well known. Various programs and alignment algorithms are described in, for example: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237-44; Higgins and Sharp (1989) *CABIOS* 5:151-3; Corpet et al. (1988) *Nucleic Acids Res.* 16:10881-90; Huang et al. (1992) *Comp. Appl. Biosci.* 8:155-65; Pearson et al. (1994) *Methods Mol. Biol.* 24:307-31; Tatiana et al. (1999) *FEMS Microbiol. Lett.* 174:247-50.

The National Center for Biotechnology Information (NCBI) Basic Local Alignment Search Tool (BLAST™; Altschul et al. (1990) *J. Mol. Biol.* 215:403-10) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

As used herein, the term "operably linked" refers to two components that have been placed into a functional relationship with one another. The term, "operably linked", when used in reference to a regulatory sequence and a coding sequence, means that the regulatory sequence affects the expression of the linked coding sequence. "Regulatory sequences", "regulatory elements", or "control elements", refer to nucleic acid sequences that influence the timing and level/amount of transcription, RNA processing or stability, or translation of the associated coding sequence. Regulatory sequences may include promoters; translation leader sequences; 5' and 3' untranslated regions, introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule. Linking can be accomplished by ligation at convenient restriction sites. If such sites do not exist, synthetic oligonucleotide adaptors or linkers are used in accordance with conventional practice. However, elements need not be contiguous to be operably linked.

As used herein, the term "transformation" encompasses all techniques by which a nucleic acid molecule can be introduced into such a cell. Examples include, but are not limited to: transfection with viral vectors; transformation with plasmid vectors; electroporation; lipofection; microinjection (Mueller et al. (1978) Cell 15:579-85); Agrobacterium-mediated transfer; direct DNA uptake; WHISKERS®-mediated transformation; and microprojectile bombardment. Transformation may be stable, wherein the nucleic acid molecule is integrated within the genome of the plant, and is subsequently passed from generation to generation. Comparatively, transformation may be transient, wherein the nucleic acid molecule is localized within the cytoplasm or nucleus of the cell and is not integrated within the genome of the plant. Such a transient transformant may result in the expression of protein or a gene product from coding sequences present on the nucleic acid molecule.

As used herein, the term "transduce" refers to a process where a virus transfers nucleic acid into a cell.

The terms "polylinker" or "multiple cloning site" as used herein defines a cluster of one or more Type -2 restriction enzyme sites. Adjacent restriction sites may be included in a polylinker and are typically located within 10 nucleotides of one another on a nucleic acid sequence. Constructs comprising a polylinker are utilized for the insertion and/or excision of nucleic acid sequences such as the coding region of a gene, a ribosomal binding sequence, an intron, or a 5'-UTR.

As used herein, the terms "restriction endonucleases" and "restriction enzymes" refer to bacterial enzymes, each of which cut double-stranded DNA at or near a specific nucleotide sequence. Type -2 restriction enzymes recognize and cleave DNA at the same site, and include but are not limited to XbaI, BamHI, HindIII, EcoRI, XhoI, SalI, KpnI, AvaI, PstI and SmaI.

The term "vector" is used interchangeably with the terms "construct", "cloning vector" and "expression vector" and means the vehicle by which a DNA or RNA sequence (e.g. a foreign gene) can be introduced into a host cell, so as to transform the host and promote expression (e.g. transcription and translation) of the introduced sequence. A "non-viral vector" is intended to mean any vector that does not comprise a virus or retrovirus. In some embodiments a "vector" is a sequence of DNA comprising at least one origin of DNA replication and at least one selectable marker gene. Examples include, but are not limited to, a plasmid, cosmid, bacteriophage, bacterial artificial chromosome (BAC), or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector. The term "plasmid" defines a circular strand of nucleic acid capable of autosomal replication in either a prokaryotic or a eukaryotic host cell. The term includes nucleic acid which may be either DNA or RNA and may be single- or double-stranded. The plasmid of the definition may also include the sequences which correspond to a bacterial origin of replication.

The term "selectable marker gene" as used herein defines a gene or other expression cassette which encodes a protein which facilitates identification of cells into which the selectable marker gene is inserted. For example a "selectable marker gene" encompasses reporter genes as well as genes used in plant transformation to, for example, protect plant cells from a selective agent or provide resistance/tolerance to a selective agent. In one embodiment only those cells or plants that receive a functional selectable marker are capable of dividing or growing under conditions having a selective agent. Examples of selective agents can include, for example, antibiotics, including spectinomycin, neomycin, kanamycin, paromomycin, gentamicin, and hygromycin. These selectable markers include neomycin phosphotransferase (npt II), which expresses an enzyme conferring resistance to the antibiotic kanamycin, and genes for the related antibiotics neomycin, paromomycin, gentamicin, and G418, or the gene for hygromycin phosphotransferase (hpt), which expresses an enzyme conferring resistance to hygromycin. Other selectable marker genes can include genes encoding herbicide resistance including bar or pat (resistance against glufosinate ammonium or phosphinothricin), acetolactate synthase (ALS, resistance against inhibitors such as sulfonylureas (SUs), imidazolinones (IMIs), triazolopyrimidines (TPs), pyrimidinyl oxybenzoates (POBs), and sulfonylamino carbonyl triazolinones that prevent the first step in the synthesis of the branched-chain amino acids), glyphosate, 2,4-D, and metal resistance or sensitivity. Examples of "reporter genes" that can be used as a selectable marker gene include the visual observation of expressed reporter gene proteins such as proteins encoding β-glucuronidase (GUS), luciferase, green fluorescent protein (GFP), yellow fluorescent protein (YFP), DsRed, β-galactosidase, chloramphenicol acetyltransferase (CAT), alkaline phosphatase, and the like. The phrase "marker-positive" refers to plants that have been transformed to include a selectable marker gene.

As used herein, the term "detectable marker" refers to a label capable of detection, such as, for example, a radioisotope, fluorescent compound, bioluminescent compound, a chemiluminescent compound, metal chelator, or enzyme. Examples of detectable markers include, but are not limited to, the following: fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In an embodiment, a detectable marker can be attached by spacer arms of various lengths to reduce potential steric hindrance.

As used herein, the term "detecting" is used in the broadest sense to include both qualitative and quantitative measurements of a specific molecule, for example, measurements of a specific polypeptide.

As used herein, the terms "cassette", "expression cassette" and "gene expression cassette" refer to a segment of DNA that can be inserted into a nucleic acid or polynucleotide at specific restriction sites or by homologous recombination. A segment of DNA comprises a polynucleotide that encodes a polypeptide of interest, and the cassette and restriction sites are designed to ensure insertion of the cassette in the proper reading frame for transcription and translation. In an embodiment, an expression cassette can include a polynucleotide that encodes a polypeptide of interest and having elements in addition to the polynucleotide that facilitate transformation of a particular host cell. In an embodiment, a gene expression cassette may also include elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein a "linker" or "spacer" is a bond, molecule or group of molecules that binds two separate entities to one another. Linkers and spacers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein, the term "control" refers to a sample used in an analytical procedure for comparison purposes. A control can be "positive" or "negative". For example, where the purpose of an analytical procedure is to detect a differentially expressed transcript or polypeptide in cells or tissue, it is generally preferable to include a positive control, such as a sample from a known plant exhibiting the desired expression, and a negative control, such as a sample from a known plant lacking the desired expression.

As used herein, the term "plant" includes a whole plant and any descendant, cell, tissue, or part of a plant. A class of plant that can be used in the present invention is generally as broad as the class of higher and lower plants amenable to mutagenesis including angiosperms (monocotyledonous and dicotyledonous plants), gymnosperms, ferns and multicellular *algae*. Thus, "plant" includes dicot and monocot plants. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

The term "protoplast", as used herein, refers to a plant cell that had its cell wall completely or partially removed, with the lipid bilayer membrane thereof naked, and thus includes protoplasts, which have their cell wall entirely removed, and spheroplasts, which have their cell wall only partially removed, but is not limited thereto. Typically, a protoplast is an isolated plant cell without cell walls which has the potency for regeneration into cell culture or a whole plant.

Unless otherwise specifically explained, all technical and scientific terms used herein have the same meaning as commonly understood by those of ordinary skill in the art to which this disclosure belongs. Definitions of common terms in molecular biology can be found in, for example: Lewin, Genes V, Oxford University Press, 1994 (ISBN 0-19-854287-9); Kendrew et al. (eds.), The Encyclopedia of Molecular Biology, Blackwell Science Ltd., 1994 (ISBN 0-632-02182-9); and Meyers (ed.), Molecular Biology and Biotechnology: A Comprehensive Desk Reference, VCH Publishers, Inc., 1995 (ISBN 1-56081-569-8).

EMBODIMENTS

As disclosed herein novel recombinant constructs are provided for expressing a non-chlorophyll a/b transgene using the regulatory sequences of a chlorophyll a/b gene from *Zea mays*. These constructs can be used to transform cells, including plant cells, to produce complete organisms that express the transgene gene product in their cells.

Plant promoters used for basic research or biotechnological application are generally unidirectional, directing only one gene that has been fused at its 3' end (downstream). It is often necessary to introduce multiple genes into plants for metabolic engineering and trait stacking and therefore, multiple promoters are typically required in transgenic crops to drive the expression of multiple genes.

Development of transgenic products is becoming increasingly complex, which requires stacking multiple transgenes into a single locus. Traditionally, each transgene usually requires a promoter for expression wherein multiple promoters are required to express different transgenes within one gene stack. This frequently leads to repetitive use of the same promoter within one transgene stack to obtain similar levels of expression patterns of different transgenes for expression of a single polygenic trait. Multi-gene constructs driven by the same promoter are known to cause gene silencing resulting in less efficacious transgenic products in the field. Excess of transcription factor (TF)-binding sites due to promoter repetition can cause depletion of endogenous TFs leading to transcriptional inactivation. The silencing of transgenes will likely undesirably affect performance of a transgenic plant produced to express transgenes. Repetitive sequences within a transgene may lead to gene intra locus homologous recombination resulting in polynucleotide rearrangements.

Moreover, tissue specific (i.e., tissue-preferred) or organ specific promoters drive gene expression in a certain tissue such as in the kernel, root, leaf or tapetum of the plant. Tissue and developmental stage specific promoters derive the expression of genes, which are expressed in particular tissues or at particular time periods during plant development. Tissue specific promoters are required for certain applications in the transgenic plants industry and are desirable as they permit specific expression of heterologous genes in a tissue and/or developmental stage selective manner, indicating expression of the heterologous gene differentially at a various organs, tissues and/or times, but not in other. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene in plant tissues that are in a particular growth or developmental phase such as, for example, cell division or elongation. Another application is the desirability of using tissue specific promoters, e.g. such that would confine the expression of the transgenes encoding an agronomic trait in developing xylem. One particular problem remaining in the identification of tissue specific promoters is how to identify the potentially most important genes and their corresponding promoters, and to relate these to specific developmental properties of the cell. Another problem is to clone all relevant cis-acting transcriptional control elements so that the cloned DNA fragment drives transcription in the wanted specific expression pattern. A particular problem is to identify tissue-specific promoters, related to specific cell types, developmental stages and/or functions in the plant that are not expressed in other plant tissues.

It is desirable to use diversified promoters for the expression of different transgenes in a gene stack. In an embodiment, regulatory elements obtained from the *Zea mays* plant species can drive transcription of multiple transcription units, including transgenes, RNAi, artificial miRNA, or hairpin-loop RNA sequences. As a further embodiment, a chlorophyll a/b promoter can be obtained from *Zea mays* to drive transcription of multiple transcription units, including a transgene, RNAi, artificial miRNA, or hairpin-loop RNA sequences. In yet another embodiment, a chlorophyll a/b promoter can be obtained from *Zea mays* to drive transcription of multiple transcription units, including a transgene, RNAi, artificial miRNA, or hairpin-loop RNA sequences in leaf, cob, silk, kernel, stem, husk and pollen tissues of a plant.

Provided are methods and constructs using gene regulatory elements isolated from *Zea mays* to express transgenes in plant. In an embodiment, a *Zea mays* promoter can be an isolated promoter of SEQ ID NO:1.

In an embodiment, a nucleic acid vector (i.e., construct) is provided comprising a promoter. In an embodiment, a promoter can be a *Zea mays* gene promoter. In an embodiment, a nucleic acid vector is provided comprising a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1. In an embodiment, a nucleic acid vector comprises a *Zea mays* gene promoter that is operably linked to a polylinker. In an embodiment, a gene expression cassette is provided comprising a *Zea mays* promoter that is operably linked to a non-chlorophyll a/b transgene. In one embodiment the promoter consists of SEQ ID NO: 1. In an illustrative embodiment, a gene expression cassette comprises a *Zea mays* promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In addition to a promoter, a 3'-untranslated gene region (i.e., 3'UTR) or terminator is needed for transcription termination and polyadenylation of the mRNA. Proper transcription termination and polyadenylation of mRNA is important for stable expression of transgene. The transcription termination becomes more critical for multigene stacks to avoid transcription read-through into next transgene. Similarly, non-polyadenylated aberrant RNA (aRNA) is a substrate for plant RNA-dependent RNA polymerases (RdRPs) to convert aRNA into double stranded RNA (dsRNA) leading to small RNA production and transgene silencing. Strong transcription terminators therefore are very useful both for single gene and multiple gene stacks. While a promoter is necessary to drive transcription, a 3'-UTR gene region can terminate transcription and initiate polyadenylation of a resulting mRNA transcript for translation and protein synthesis. A 3'-UTR gene region aids stable expression of a transgene.

In accordance with one embodiment a nucleic acid construct is provided comprising a *Zea mays* transcription terminator. In an embodiment, the *Zea mays* transcription terminator is provided comprising a transcription terminator, wherein the transcription terminator is at least 80%, 85%, 90%, 91%, 92%, 93%, 94%, 95%, 96%, 97%, 98%, 99%, 99.5%, 99.8%, or 100% identical to SEQ ID NO:6. In an embodiment, a nucleic acid construct is provided comprising a *Zea mays* transcription terminator that is operably linked to a polylinker. In an embodiment, a gene expression cassette is provided comprising a *Zea mays* transcription terminator that is operably linked to the 3' end of a non-chlorophyll a/b transgene. In one embodiment the transcription terminator consists of SEQ ID NO:6. In an illustrative embodiment, a gene expression cassette comprises a *Zea mays* transcription terminator that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In one embodiment a nucleic acid vector is provided comprising a transcription terminator operably linked to either a polylinker sequence, a non-chlorophyll a/b transgene or a combination of both, wherein the transcription terminator comprises SEQ ID NO:6 or a sequence that has 90% sequence identity with SEQ ID NO:6. In one embodiment the transcription terminator is less than 1 kb in length, and in a further embodiment the transcription terminator consists of the 3'UTR sequence of SEQ ID NO:6.

In an embodiment, a nucleic acid construct is provided comprising a *Zea mays* promoter as described herein and a 3'-UTR. In an embodiment, the nucleic acid construct comprises a *Zea mays* 3'-UTR. In an embodiment, the *Zea mays* 3'-UTR is a *Zea mays* 3'-UTR. In an embodiment, a 3'-UTR can be the *Zea mays* 3'-UTR of SEQ ID NO:6.

In an embodiment, a nucleic acid construct is provided comprising a *Zea mays* promoter as described herein and a 3'-UTR, wherein the 3'-UTR is at least 80%, 85%, 90%, 91%, 92%, 93%, 94%, 95%, 96%, 97%, 98%, 99%, 99.5%, 99.8%, or 100% identical to SEQ ID NO:6. In an embodiment, a nucleic acid construct is provided comprising a *Zea mays* promoter as described herein and the 3'-UTR wherein the *Zea mays* promoter and 3'-UTR are both operably linked to opposite ends of a polylinker. In an embodiment, a gene expression cassette is provided comprising a *Zea mays* promoter as described herein and a 3'-UTR, wherein the *Zea mays* promoter and 3'-UTR are both operably linked to opposite ends of a non-chlorophyll a/b transgene. In one embodiment the a 3'-UTR, consists of SEQ ID NO:6. In one embodiment, a gene expression cassette is provided comprising a *Zea mays* promoter as described herein and a 3'-UTR, wherein the *Zea mays* promoter comprises SEQ ID NO:1 and the 3'-UTR comprises SEQ ID NO:6 wherein the promoter and 3'-UTR are operably linked to opposite ends of a non-cholorophyll a/b transgene. In one embodiment the a 3'-UTR, consists of SEQ ID NO:6. In one embodiment the promoter consists of SEQ ID NO:1 or SEQ ID NO:5 and the 3'-UTR, consists of SEQ ID NO:6. In an illustrative embodiment, a gene expression cassette comprises a *Zea mays* 3'-UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In a further embodiment the transgene is operably linked to a *Zea mays* promoter and a 3'-UTR from the same gene isolated from *Zea mays*.

In one embodiment a vector is provided comprising a first transgene and/or polylinker and a second transgene and/or polylinker wherein the first transgene and/or polylinker is operably linked to a promoter comprising a sequence selected from the group consisting of SEQ ID NO:1 and SEQ ID NO:5 and operably linked to a 3'-UTR, comprising a sequence selected from the group consisting of SEQ ID NO:6.

Transgene expression may also be regulated by an intron region located downstream of the promoter sequence. Both a promoter and an intron can regulate transgene expression. While a promoter is necessary to drive transcription, the presence of an intron can increase expression levels resulting in mRNA transcript for translation and protein synthesis. An intron gene region aids stable expression of a transgene.

In an embodiment, a nucleic acid construct is provided comprising a *Zea mays* promoter as described herein and an intron. In one embodiment the intron is operably linked to the 3' end of the promoter. In an embodiment, a nucleic acid construct is provided comprising a *Zea mays* intron operably linked to the 3' end of a *Zea mays* promoter or a derivative of such promoter sequence. In an embodiment, the *Zea mays* intron is a *Zea mays* chlorophyll a/b intron, or a derivative of such intron sequence.

In an embodiment, an intron can be the *Zea mays* chlorophyll a/b intron of SEQ ID NO:2. In another embodiment, an intron can be the *Zea mays* chlorophyll a/b intron of SEQ ID NO:3. In an embodiment, a nucleic acid construct is provided comprising a *Zea mays* promoter as described herein and an intron, wherein the intron is at least 80%, 85%, 90%, 91%, 92%, 93%, 94%, 95%, 96%, 97%, 98%, 99%, 99.5%, 99.8%, or 100% identical to SEQ ID NO:2 or SEQ ID NO:3. In an embodiment, a nucleic acid construct is provided comprising a *Zea mays* promoter as described herein, an intron sequence and a polylinker wherein the promoter and intron are operably linked to a polylinker. In an embodiment, a gene expression cassette is provided comprising a *Zea mays* promoter as described herein, an intron sequence and a non-chlorophyll a/b transgene wherein the promoter and intron are operably linked to the 5' end of the transgene. Optionally the construct further comprises a 3'-UTR that is operably linked to the 3' end of the non-chlorophyll a/b transgene or polylinker. In one embodiment the promoter and 3'-UTR sequences are selected from those described herein and the intron sequence consists of SEQ ID NO:2 or SEQ ID NO:3. In an embodiment, a gene expression cassette comprises a *Zea mays* intron that is operably linked to a promoter, wherein the promoter is a *Zea mays* promoter of SEQ ID NO:1, or a promoter that originates from a plant (e.g., *Zea mays* ubiquitin 1 promoter), a virus (e.g., Cassava vein mosaic virus promoter) or a bacteria (e.g., *Agrobacterium tumefaciens* delta mas). In an illustrative embodiment, a gene expression cassette comprises a *Zea mays* intron that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

Transgene expression may also be regulated by a 5'-UTR region located downstream of the promoter sequence. Both a promoter and a 5'-UTR can regulate transgene expression. While a promoter is necessary to drive transcription, the presence of a 5'-UTR can increase expression levels resulting in mRNA transcript for translation and protein synthesis. A 5'-UTR gene region aids stable expression of a transgene.

In an embodiment, a nucleic acid construct is provided comprising a *Zea mays* promoter as described herein and a 5'-UTR. In one embodiment the 5'-UTR is operably linked to the 3' end of the promoter. In an embodiment, a nucleic acid construct is provided comprising a *Zea mays* 5'-UTR operably linked to the 3' end of a chlorophyll a/b promoter isolated from *Panicum Zea mays* or a derivative of such promoter sequence. In a further embodiment the 3' end of the 5'-UTR is operably linked to the 5' end of a *Zea mays* intron, as described herein.

In an embodiment, a 5'-UTR can be the *Zea mays* 5'-UTR of SEQ ID NO:4. In an embodiment, a nucleic acid construct is provided comprising a *Zea mays* promoter as disclosed herein and a 5'-UTR, wherein the 5'-UTR is at least 80%, 85%, 90%, 91%, 92%, 93%, 94%, 95%, 96%, 97%, 98%, 99%, 99.5%, 99.8%, or 100% identical SEQ ID NO:4. In an embodiment, a nucleic acid construct is provided comprising *Zea mays* promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:4, and a 5'-UTR operably linked to a polylinker. In an embodiment, a gene expression cassette is provided comprising a *Zea mays* promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:4, and a 5'-UTR sequences operably linked to a non-chlorophyll a/b transgene. Optionally, the construct can further comprise a *Zea mays* intron as disclosed herein operably linked to the 3' end of the 5'-UTR and the 5' end of the non-chlorophyll a/b transgene and optionally further comprising a 3'-UTR that is operably linked to the 3' end of the non-chlorophyll a/b transgene. In one embodiment the promoter, intron and 3'-UTR sequences are selected from those described herein and the 5'-UTR sequence consists of SEQ ID NO:4. In one embodiment the 3'-UTR consists of SEQ ID NO:6.

In an embodiment, a gene expression cassette comprises a *Zea mays* 5'-UTR that is operably linked to a promoter, wherein the promoter is a *Zea mays* promoter of SEQ ID NO:1, or a promoter that originates from a plant (e.g., *Zea mays* ubiquitin 1 promoter), a virus (e.g., Cassava vein mosaic virus promoter) or a bacteria (e.g., *Agrobacterium tumefaciens* delta mas). In an illustrative embodiment, a gene expression cassette comprises a *Zea mays* 5'-UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In one embodiment a nucleic acid construct is provided comprising a promoter and a polylinker and optionally one or more of the following elements:
a) a 5' untranslated region;
b) an intron; and
c) a 3' untranslated region, wherein
the promoter consists of SEQ ID NO:1 or a sequence having 98% sequence identity with SEQ ID NO:1;
the 5' untranslated region consists of SEQ ID NO:4 or a sequence having 98% sequence identity with SEQ ID NO:4;
the intron consists of SEQ ID NO:2, or SEQ ID NO:3 or a sequence having 98% sequence identity with SEQ ID NO:2, or SEQ ID NO:3;
the 3' untranslated region consists of SEQ ID NO:6 or a sequence having 98% sequence identity with SEQ ID NO:6;
further wherein said promoter is operably linked to said polylinker and each optional element, when present, is also operably linked to both the promoter and the polylinker.

In one embodiment a nucleic acid construct is provided comprising a promoter and a non-chlorophyll a/b transgene and optionally one or more of the following elements:
a) a 5' untranslated region;
b) an intron; and
c) a 3' untranslated region,
wherein
the promoter consists of SEQ ID NO:1 or a sequence having 98% sequence identity with SEQ ID NO:1;
the 5' untranslated region consists of SEQ ID NO:4 or a sequence having 98% sequence identity with SEQ ID NO:4;
the intron consists of SEQ ID NO:2, or SEQ ID NO:3 or a sequence having 98% sequence identity with SEQ ID NO:2, or SEQ ID NO:3;
the 3' untranslated region consists of SEQ ID NO:6, or a sequence having 98% sequence identity with SEQ ID NO:6;
further wherein said promoter is operably linked to said transgene and each optional element, when present, is also operably linked to both the promoter and the transgene. In a further embodiment a transgenic cell is provided comprising the nucleic acid construct disclosed immediately above. In one embodiment the transgenic cell is a plant cell, and in a further embodiment a plant is provided wherein the plant comprises said transgenic cells.

In accordance with one embodiment transgene expression is regulated by a promoter operably linked to an intron and 5'-UTR region, wherein the intron and 5'-UTR region are located downstream of the promoter sequence. A promoter operably linked to an intron and 5'-UTR region can be used to drive transgene expression. While a promoter is necessary to drive transcription, the presence of the intron and 5'-UTR can increase expression levels resulting in mRNA transcript for translation and protein synthesis.

In an embodiment, a gene expression cassette comprises a promoter operably linked to a 5'-UTR and intron region. In an embodiment, a gene expression cassette comprises a *Zea mays* promoter operably linked to a *Zea mays* 5'-UTR and *Zea mays* intron. In an embodiment, the *Zea mays* promoter operably linked to a 5'-UTR and intron region is operably linked to an intron and 5'-UTR.

In an embodiment, a promoter operably linked to a 5'-UTR and intron can be the *Zea mays* promoter operably linked to an intron and 5'-UTR. In one embodiment the promoter comprises or consists of the sequence of SEQ ID NO:5. In an embodiment, a nucleic acid construct is provided comprising a promoter operably linked to an intron and 5'-UTR. In one embodiment the construct comprises at least 80%, 85%, 90%, 91%, 92%, 93%, 94%, 95%, 96%, 97%, 98%, 99%, 99.5%, 99.8%, or 100% identical to SEQ ID NO:5. In one embodiment, a nucleic acid construct is provided comprising a *Zea mays* promoter sequence comprising or consisting of a sequence at least 80%, 85%, 90%, 91%, 92%, 93%, 94%, 95%, 96%, 97%, 98%, 99%, 99.5%, 99.8%, or 100% identical to SEQ ID NO:5 operably linked to a polylinker. Optionally, the construct can further comprise 3'-UTR that is operably linked to the 3' end of the polylinker. In an embodiment, a gene expression cassette is provided comprising a *Zea mays* promoter sequence wherein the promoter sequence comprises or consists of a sequence at least 80%, 85%, 90%, 91%, 92%, 93%, 94%, 95%, 96%, 97%, 98%, 99%, 99.5%, 99.8%, or 100% identical to SEQ ID NO:5 operably linked to a non-chlorophyll a/b transgene. Optionally, the construct can further comprise 3'-UTR that is operably linked to the 3' end of the non-chlorophyll a/b transgene. In one embodiment the 3'-UTR sequence consists of SEQ ID NO:6. In an illustrative embodiment, the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In one embodiment the transgene is an herbicide resistance gene. In one embodiment a vector is provided comprising 1, 2, 3 or 4 promoter sequences independently selected from the group consisting of SEQ ID NO:1 or SEQ ID NO:5.

In an embodiment, a gene expression cassette comprises a *Zea mays* promoter, a *Zea mays* 5'-UTR, a *Zea mays* intron, and a *Zea mays* 3'-UTR. In an embodiment, a gene expression cassette comprises: a) a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1; b) a 3'-UTR, wherein the 3'-UTR is at least 80%, 85%, 90%, 91%, 92%, 93%, 94%, 95%, 96%, 97%, 98%, 99%, 99.5%, 99.8%, or 100% identical to SEQ ID NO:6; c) a 5'-UTR, wherein the 5'-UTR is at least 80%, 85%, 90%, 91%, 92%, 93%, 94%, 95%, 96%, 97%, 98%, 99%, 99.5%, 99.8%, or 100% identical to SEQ ID NO:4; or, d) an intron, wherein the intron is at least 80%, 85%, 90%, 91%, 92%, 93%, 94%, 95%, 96%, 97%, 98%, 99%, 99.5%, 99.8%, or 100% identical to SEQ ID NO:2, or SEQ ID NO:3.

For example, a gene expression cassette may include both a promoter, an intron, and a 5'-UTR wherein the promoter is a polynucleotide of SEQ ID NO:1, the intron is a polynucleotide of SEQ ID NO:2 or SEQ ID NO:3, and the 5'-UTR is a polynucleotide of SEQ ID NO:4. Furthermore, a gene expression cassette may include both a promoter, an intron, a 5'-UTR, and a 3'-UTR wherein the promoter is a polynucleotide of SEQ ID NO:1, the intron is a polynucleotide of SEQ ID NO:2 or SEQ ID NO:3, the 5'-UTR is a polynucleotide of SEQ ID NO:4, and the 3'-UTR is a polynucleotide of SEQ ID NO:6. In addition, a gene expression cassette may include both a promoter, and a 3'-UTR wherein the promoter is a polynucleotide of SEQ ID NO:1 and a 3'-UTR of SEQ ID NO:6

In an embodiment, a gene expression cassette comprises a *Zea mays* promoter, *Zea mays* 5'-UTR, and a *Zea mays* 3'-UTR that are operably linked to a non-chlorophyll a/b transgene.

A promoter, an intron, a 5'-UTR, and 3'-UTR can be operably linked to different transgenes within a gene expression cassette when a gene expression cassette includes one or more transgenes. In an illustrative embodiment, a gene expression cassette comprises a *Zea mays* promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In an illustrative embodiment, a gene expression cassette comprises a *Zea mays* promoter, a *Zea*

*mays* intron, and a *Zea mays* 5'-UTR that are operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In an illustrative embodiment, a gene expression cassette comprises a *Zea mays* 3'-UTR that is operably linked to a transgene, wherein the transgene encodes for a gene product that enhances insecticidal resistance, herbicide tolerance, nitrogen use efficiency, water use efficiency, nutritional quality or combinations thereof.

A *Zea mays* intron and a 5'-UTR can be operably linked to different promoters within a gene expression cassette. In an illustrative embodiment, the promoters originate from a plant (e.g., *Zea mays* ubiquitin 1 promoter), a virus (e.g., Cassava vein mosaic virus promoter) or a bacteria (e.g., *Agrobacterium tumefaciens* delta mas). In an illustrative embodiment, a gene expression cassette comprises a *Zea mays* promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, a vector comprises a gene expression cassette as disclosed herein. In an embodiment, a vector can be a plasmid, a cosmid, a bacterial artificial chromosome (BAC), a bacteriophage, a virus, or an excised polynucleotide fragment for use in direct transformation or gene targeting such as a donor DNA.

In accordance with one embodiment a nucleic acid vector is provided comprising a recombinant gene cassette wherein the recombinant gene cassette comprises a *Zea mays* promoter of SEQ ID NO:1 operably linked to a polylinker sequence, a non-chlorophyll a/b transgene or combination thereof. In one embodiment the recombinant gene cassette comprises a *Zea mays* promoter of SEQ ID NO:1 operably linked to a non-chlorophyll a/b transgene. In one embodiment the recombinant gene cassette comprises a *Zea mays* promoter of SEQ ID NO:1 as disclosed herein operably linked to a polylinker sequence. The polylinker is operably linked to the a *Zea mays* promoter of SEQ ID NO:1 in a manner such that insertion of a coding sequence into one of the restriction sites of the polylinker will operably link the coding sequence allowing for expression of the coding sequence when the vector is transfected into a host cell.

In accordance with one embodiment the *Zea mays* promoter comprises SEQ ID NO:1 or a sequence that has 90, 95 or 99% sequence identity with SEQ ID NO: 35. In accordance with one embodiment the promoter sequence has a total length of no more than 1.5, 2, 2.5, 3 or 4 kb. In accordance with one embodiment the *Zea mays* promoter consists of SEQ ID NO: 1 or about a 379 bp sequence that has 90, 95 or 99% sequence identity with SEQ ID NO:1.

In accordance with one embodiment a nucleic acid vector is provided comprising a gene cassette that consists of SEQ ID NO:1, a non-chlorophyll a/b transgene and a 3'-UTR, wherein SEQ ID NO:1 is operably linked to the 5' end of the non-chlorophyll a/b transgene and the 3'-UTR is operably linked to the 3' end of the non-chlorophyll a/b transgene. In a further embodiment the 3' untranslated sequence comprises SEQ ID NO:6 or a sequence that has 90, 95, 99 or 100% sequence identity with SEQ ID NO:6. In a further embodiment the 3' untranslated sequence consists of SEQ ID NO:6, or about a 295 bp sequence that has 90, 95, or 99% sequence identity with SEQ ID NO:6.

In accordance with one embodiment the nucleic acid vector further comprises a sequence encoding a selectable maker. In accordance with one embodiment the recombinant gene cassette is operably linked to an *Agrobacterium* T-DNA border. In accordance with one embodiment the recombinant gene cassette further comprises a first and second T-DNA border, wherein first T-DNA border is operably linked to one end of the gene construct, and said second T-DNA border is operably linked to the other end of the gene construct. The first and second *Agrobacterium* T-DNA borders can be independently selected from T-DNA border sequences originating from bacterial strains selected from the group consisting of a nopaline synthesizing *Agrobacterium* T-DNA border, an ocotopine synthesizing *Agrobacterium* T-DNA border, a succinamopine synthesizing *Agrobacterium* T-DNA border, or any combination thereof. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene operably linked to a sequence selected from SEQ ID NO:6 or a sequence having 90, 95, or 99% sequence identity with SEQ ID NO:6.

Transgenes of interest and suitable for use in the present disclosed constructs include, but are not limited to, coding sequences that confer (1) resistance to pests or disease, (2) resistance to herbicides, and (3) value added traits as disclosed in WO2013116700 (DGT-28), US20110107455 (DSM-2), U.S. Pat. No. 8,283,522 (AAD-12); U.S. Pat. No. 7,838,733 (AAD-1); U.S. Pat. Nos. 5,188,960; 5,691,308; 6,096,708; and 6,573,240 (Cry1F); U.S. Pat. Nos. 6,114,138; 5,710,020; and 6,251,656 (Cry1Ac); U.S. Pat. Nos. 6,127,180; 6,624,145 and 6,340,593 (Cry34Ab1); U.S. Pat. Nos. 6,083,499; 6,548,291 and 6,340,593 (Cry35Ab1), the disclosures of which are incorporated herein. In accordance with one embodiment the transgene encodes a selectable marker or a gene product conferring insecticidal resistance, herbicide tolerance, nitrogen use efficiency, water use efficiency, or nutritional quality.

In an embodiment, a cell or plant is provided comprising a gene expression cassette as disclosed herein. In an embodiment, a cell or plant comprises a vector comprising a gene expression cassette as disclosed herein. In an embodiment, a vector can be a plasmid, a cosmid, a bacterial artificial chromosome (BAC), a bacteriophage, or a virus. Thereby, a cell or plant comprising a gene expression cassette as disclosed herein is a transgenic cell or transgenic plant, respectively. In an embodiment, a transgenic plant can be a monocotyledonous plant. In an embodiment, a transgenic monocotyledonous plant can be, but is not limited to maize, wheat, rice, sorghum, oats, rye, bananas, sugar cane, and millet. In an embodiment, a transgenic plant can be a dicotyledonous plant. In an embodiment, a transgenic dicotyledonous plant can be, but is not limited to soybean, cotton, sunflower, and canola. An embodiment also includes a transgenic seed from a transgenic plant as disclosed herein.

In an embodiment, a gene expression cassette includes two or more transgenes. The two or more transgenes may not be operably linked to a promoter, intron, or 5'-UTR or 3'-UTR as disclosed herein. In an embodiment, a gene expression cassette includes one or more transgenes. In an embodiment with one or more transgenes, at least one transgene is operably linked to a promoter, intron, 5'-UTR, or 3'-UTR or the subject disclosure.

Selectable Markers:

Various selectable markers also described as reporter genes can be incorporated into a chosen expression vector to allow for identification and selection of transformed plants ("transformants"). Many methods are available to confirm expression of selectable markers in transformed plants, including for example DNA sequencing and PCR (polymerase chain reaction), Southern blotting, Northern blotting, immunological methods for detection of a protein expressed from the vector, e g., precipitated protein that mediates phosphinothricin resistance, or visual observation of other proteins such as reporter genes encoding β-glucuronidase (GUS), luciferase, green fluorescent protein (GFP), yellow fluorescent protein (YFP), red fluorescent protein (RFP), β-galactosidase, alkaline phosphatase, and the like (See Sambrook, et al., Molecular Cloning: A Laboratory Manual, Third Edition, Cold Spring Harbor Press, N.Y., 2001, the content of which is incorporated herein by reference in its entirety).

Selectable marker genes are utilized for selection of transformed cells or tissues. Selectable marker genes include genes encoding antibiotic resistance, such as those encoding neomycin phosphotransferase II (NEO) and hygromycin phosphotransferase (HPT) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate has been obtained by using genes coding for mutant target enzymes, 5-enolpyruvylshikimate-3-phosphate synthase (EPSPS) or DGT-28. Genes and mutants for EPSPS are well known, and further described below. Resistance to glufosinate ammonium, bromoxynil, and 2,4-dichlorophenoxyacetate (2,4-D) have been obtained by using bacterial genes encoding pat or DSM-2, a nitrilase, an aad-1 or an aad-12 gene, which detoxifies the respective herbicides.

In an embodiment, herbicides can inhibit the growing point or meristem, including imidazolinone or sulfonylurea, and genes for resistance/tolerance of acetohydroxyacid synthase (AHAS) and acetolactate synthase (ALS) for these herbicides are well known. Glyphosate resistance genes include mutant 5-enolpyruvylshikimate-3-phosphate synthase (EPSPs) and dgt-28 genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include bar genes from Streptomyces species, including Streptomyces hygroscopicus and Streptomyces viridichromogenes, and pyridinoxy or phenoxy proprionic acids and cyclohexones (ACCase inhibitor-encoding genes). Exemplary genes conferring resistance to cyclohexanediones and/or aryloxyphenoxypropanoic acid (including Haloxyfop, Diclofop, Fenoxyprop, Fluazifop, Quizalofop) include genes of acetyl coenzyme A carboxylase (ACCase)-Acc1-S1, Acc1-S2 and Acc1-S3. In an embodiment, herbicides can inhibit photosynthesis, including triazine (psbA and 1s+ genes) or benzonitrile (nitrilase gene).

In an embodiment, selectable marker genes include, but are not limited to genes encoding: neomycin phosphotransferase II; cyanamide hydratase; aspartate kinase; dihydrodipicolinate synthase; tryptophan decarboxylase; dihydrodipicolinate synthase and desensitized aspartate kinase; bar gene; tryptophan decarboxylase; neomycin phosphotransferase (NEO); hygromycin phosphotransferase (HPT or HYG); dihydrofolate reductase (DHFR); phosphinothricin acetyltransferase; 2,2-dichloropropionic acid dehalogenase; acetohydroxyacid synthase; 5-enolpyruvyl-shikimate-phosphate synthase (aroA); haloarylnitrilase; acetyl-coenzyme A carboxylase; dihydropteroate synthase (sul I); and 32 kD photosystem II polypeptide (psbA).

An embodiment also includes genes encoding resistance to: chloramphenicol; methotrexate; hygromycin; spectinomycin; bromoxynil; glyphosate; and phosphinothricin.

The above list of selectable marker genes is not meant to be limiting. Any reporter or selectable marker gene are encompassed by the present invention.

Selectable marker genes are synthesized for optimal expression in a plant. For example, in an embodiment, a coding sequence of a gene has been modified by codon optimization to enhance expression in plants. A selectable marker gene can be optimized for expression in a particular plant species or alternatively can be modified for optimal expression in dicotyledonous or monocotyledonous plants. Plant preferred codons may be determined from the codons of highest frequency in the proteins expressed in the largest amount in the particular plant species of interest. In an embodiment, a selectable marker gene is designed to be expressed in plants at a higher level resulting in higher transformation efficiency. Methods for plant optimization of genes are well known. Guidance regarding the optimization and production of synthetic DNA sequences can be found in, for example, WO2013016546, WO2011146524, WO1997013402, U.S. Pat. No. 6,166,302, and U.S. Pat. No. 5,380,831, herein incorporated by reference. Transformation;

Suitable methods for transformation of plants include any method by which DNA can be introduced into a cell, for example and without limitation: electroporation (see, e.g., U.S. Pat. No. 5,384,253); micro-projectile bombardment (see, e.g., U.S. Pat. Nos. 5,015,580, 5,550,318, 5,538,880, 6,160,208, 6,399,861, and 6,403,865); Agrobacterium-mediated transformation (see, e.g., U.S. Pat. Nos. 5,635,055, 5,824,877, 5,591,616; 5,981,840, and 6,384,301); and protoplast transformation (see, e.g., U.S. Pat. No. 5,508,184). These methods may be used to stably transform or transiently transform a plant.

A DNA construct may be introduced directly into the genomic DNA of the plant cell using techniques such as agitation with silicon carbide fibers (See, e.g., U.S. Pat. Nos. 5,302,523 and 5,464,765), or the DNA constructs can be introduced directly to plant tissue using biolistic methods, such as DNA particle bombardment (see, e.g., Klein et al. (1987) Nature 327:70-73). Alternatively, the DNA construct can be introduced into the plant cell via nanoparticle transformation (see, e.g., US Patent Publication No. 20090104700, which is incorporated herein by reference in its entirety).

In addition, gene transfer may be achieved using non-Agrobacterium bacteria or viruses such as Rhizobium sp. NGR234, Sinorhizoboium meliloti, Mesorhizobium loti, potato virus X, cauliflower mosaic virus and cassava vein mosaic virus and/or tobacco mosaic virus, See, e.g., Chung et al. (2006) Trends Plant Sci. 11(1):1-4.

Through the application of transformation techniques, cells of virtually any plant species may be stably transformed, and these cells may be developed into transgenic plants by well-known techniques. For example, techniques that may be particularly useful in the context of cotton transformation are described in U.S. Pat. Nos. 5,846,797, 5,159,135, 5,004,863, and 6,624,344; techniques for transforming Brassica plants in particular are described, for example, in U.S. Pat. No. 5,750,871; techniques for transforming soy bean are described, for example, in U.S. Pat. No. 6,384,301; and techniques for transforming maize are described, for example, in U.S. Pat. Nos. 7,060,876 and 5,591,616, and International PCT Publication WO 95/06722.

After effecting delivery of an exogenous nucleic acid to a recipient cell, a transformed cell is generally identified for further culturing and plant regeneration. In order to improve the ability to identify transformants, one may desire to employ a selectable marker gene with the transformation vector used to generate the transformant. In an illustrative embodiment, a transformed cell population can be assayed by exposing the cells to a selective agent or agents, or the cells can be screened for the desired marker gene trait.

Cells that survive exposure to a selective agent, or cells that have been scored positive in a screening assay, may be cultured in media that supports regeneration of plants. In an embodiment, any suitable plant tissue culture media may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of a desired nucleic acid comprising constructs provided in regenerating plants, a variety of assays may be performed. Such assays may include: molecular biological assays, such as Southern and northern blotting and PCR; biochemical assays, such as detecting the presence of a protein product, e.g., by immunological means (ELISA, western blots, and/or LC-MS MS spectrophotometry) or by enzymatic function; plant part assays, such as leaf or root assays; and/or analysis of the phenotype of the whole regenerated plant.

Transgenic events may be screened, for example, by PCR amplification using, e.g., oligonucleotide primers specific for nucleic acid molecules of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (see, e.g., Rios et al. (2002) Plant J. 32:243-53), and may be applied to genomic DNA derived from any plant species or tissue type, including cell cultures. Combinations of oligonucleotide primers that bind to both target sequence and introduced sequence may be used sequentially or multiplexed in PCR amplification reactions. Oligonucleotide primers designed to anneal to the target site, introduced nucleic acid sequences, and/or combinations of the two may be produced. Thus, PCR genotyping strategies may include, for example and without limitation: amplification of specific sequences in the plant genome; amplification of multiple specific sequences in the plant genome; amplification of non-specific sequences in the plant genome; and combinations of any of the foregoing. One skilled in the art may devise additional combinations of primers and amplification reactions to interrogate the genome. For example, a set of forward and reverse oligonucleotide primers may be designed to anneal to nucleic acid sequence(s) specific for the target outside the boundaries of the introduced nucleic acid sequence.

Forward and reverse oligonucleotide primers may be designed to anneal specifically to an introduced nucleic acid molecule, for example, at a sequence corresponding to a coding region within a nucleotide sequence of interest comprised therein, or other parts of the nucleic acid molecule. Primers may be used in conjunction with primers described herein. Oligonucleotide primers may be synthesized according to a desired sequence and are commercially available (e.g., from Integrated DNA Technologies, Inc., Coralville, Iowa). Amplification may be followed by cloning and sequencing, or by direct sequence analysis of amplification products. In an embodiment, oligonucleotide primers specific for the gene target are employed in PCR amplifications. Method of Expressing a Transgene In an embodiment, a method of expressing at least one transgene in a plant comprises growing a plant comprising a *Zea mays* promoter operably linked to at least one transgene. In an embodiment, a method of expressing at least one transgene in a plant comprising growing a plant comprising a *Zea mays* 5'-UTR operably linked to at least one transgene. In an embodiment, a method of expressing at least one transgene in a plant comprising growing a plant comprising a *Zea mays* intron operably linked to at least one transgene. In an embodiment, a method of expressing at least one transgene in a plant comprising growing a plant comprising a *Zea mays* promoter, a *Zea mays* 5'-UTR, and a *Zea mays* intron operably linked to at least one transgene. In an embodiment, a method of expressing at least one transgene in a plant comprising growing a plant comprising a *Zea mays* 3'-UTR operably linked to at least one transgene. In an embodiment, a method of expressing at least one transgene in a plant tissue or plant cell comprising culturing a plant tissue or plant cell comprising a *Zea mays* promoter operably linked to at least one transgene. In an embodiment, a method of expressing at least one transgene in a plant tissue or plant cell comprising culturing a plant tissue or plant cell comprising a *Zea mays* 5'-UTR operably linked to at least one transgene. In an embodiment, a method of expressing at least one transgene in a plant tissue or plant cell comprising culturing a plant tissue or plant cell comprising a *Zea mays* intron operably linked to at least one transgene. In an embodiment, a method of expressing at least one transgene in a plant tissue or plant cell comprising culturing a plant tissue or plant cell comprising a *Zea mays* promoter, a *Zea mays* 5'-UTR, and a *Zea mays* intron operably linked to at least one transgene. In an embodiment, a method of expressing at least one transgene in a plant tissue or plant cell comprising culturing a plant tissue or plant cell comprising a *Zea mays* 3'-UTR operably linked to at least one transgene.

In an embodiment, a method of expressing at least one transgene in a plant comprises growing a plant comprising a gene expression cassette comprising a *Zea mays* promoter operably linked to at least one transgene. In one embodiment the *Zea mays* promoter consists of a sequence selected from SEQ ID NO:1, or a sequence that has 90, 95 or 99% sequence identity with a sequence selected from SEQ ID NO:1. In an embodiment, a method of expressing at least one transgene in a plant comprises growing a plant comprising a gene expression cassette comprising a *Zea mays* intron operably linked to at least one transgene. In an embodiment, a method of expressing at least one transgene in a plant linked to at least one transgene. In an embodiment, a method of expressing at least one transgene in a plant comprises growing a plant comprising a gene expression cassette comprising a *Zea mays* promoter, a *Zea mays* 5'-UTR, and a *Zea mays* intron operably linked to at least one transgene. In an embodiment, a method of expressing at least one transgene in a plant comprises growing a plant comprising a gene expression cassette comprising a *Zea mays* 3'-UTR operably linked to at least one transgene. In an embodiment, a method of expressing at least one transgene in a plant tissue or plant cell comprises culturing a plant tissue or plant cell comprising a gene expression cassette a *Zea mays* promoter operably linked to at least one transgene. In an embodiment, a method of expressing at least one transgene in a plant tissue or plant cell comprises culturing a plant tissue or plant cell comprising a gene expression cassette a *Zea mays* intron operably linked to at least one transgene. In an embodiment, a method of expressing at least one transgene in a plant tissue or plant cell comprises culturing a plant tissue or plant cell comprising a gene expression cassette a *Zea mays* 5'-UTR operably linked to at least one transgene. In an embodiment, a method of expressing at least one transgene in a plant tissue or plant cell comprises culturing a plant tissue or plant cell comprising a gene expression cassette a *Zea mays* promoter, a *Zea mays* 5'-UTR, and a *Zea mays* intron operably linked to at least one transgene. In an embodiment, a method of expressing at least one transgene in a plant tissue or plant cell comprises culturing a plant tissue or plant cell comprising a gene expression cassette comprising a *Zea mays* 3'-UTR operably linked to at least one transgene.

Transgenic Plants;

In an embodiment, a plant, plant tissue, or plant cell comprises a *Zea mays* promoter. In an embodiment, a *Zea mays* promoter can be a promoter of SEQ ID NO:1 or a promoter with at least 90%, 95%, or 99% sequence identity with SEQ ID NO:1. In an embodiment, a plant, plant tissue, or plant cell comprises a gene expression cassette comprises a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1, wherein the promoter is operably linked to a non-chlorophyll a/b transgene. In an embodiment, a plant, plant tissue, or plant cell comprises a gene expression cassette comprising a sequence selected from SEQ ID NO:1, or a sequence that has 90, 95 or 995 sequence identity with a sequence selected from SEQ ID NO:1 that is operably linked to a non-chlorophyll a/b transgene. In an illustrative embodiment, a plant, plant tissue, or plant cell comprises a gene expression cassette comprising a *Zea mays* promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, a plant, plant tissue, or plant cell comprises a gene expression cassette comprising a 3'-UTR. In an embodiment, a plant, plant tissue, or plant cell comprises a gene expression cassette comprising a *Zea mays* 3'-UTR.

In an embodiment, a plant, plant tissue, or plant cell comprises a gene expression cassette comprising an intron, wherein the intron is at least 80%, 85%, 90%, 91%, 92%, 93%, 94%, 95%, 96%, 97%, 98%, 99%, 99.5%, 99.8%, or 100% identical to SEQ ID NO:2 or SEQ ID NO:3. In an embodiment, a gene expression cassette comprises a *Zea mays* intron that is operably linked to a promoter, wherein the promoter is a *Zea mays* promoter of SEQ ID NO:1, or a promoter that originates from a plant (e.g., *Zea mays* ubiq- uitin 1 promoter), a virus (e.g., Cassava vein mosaic virus promoter) or a bacteria (e.g., *Agrobacterium tumefaciens* delta mas). In an embodiment, a plant, plant tissue, or plant cell comprises a gene expression cassette comprising a *Zea mays* intron that is operably linked to a transgene. In an illustrative embodiment, a plant, plant tissue, or plant cell comprising a gene expression cassette comprising a *Zea mays* intron that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, a plant, plant tissue, or plant cell comprises a gene expression cassette comprising a 5'-UTR, wherein the 5'-UTR is at least 80%, 85%, 90%, 91%, 92%, 93%, 94%, 95%, 96%, 97%, 98%, 99%, 99.5%, 99.8%, or 100% identical to SEQ ID NO:4. In an embodiment, a gene expression cassette comprises a *Zea mays* 5'-UTR that is operably linked to a promoter, wherein the promoter is a *Zea mays* promoter of SEQ ID NO:1, or a promoter that originates from a plant (e.g., *Zea mays* ubiquitin 1 promoter), a virus (e.g., Cassava vein mosaic virus promoter) or a bacteria (e.g., *Agrobacterium tumefaciens* delta mas). In an embodiment, a plant, plant tissue, or plant cell comprises a gene expression cassette comprising a *Zea mays* 5'-UTR that is operably linked to a transgene. In an illustrative embodiment, a plant, plant tissue, or plant cell comprising a gene expression cassette comprising a *Zea mays* 5'-UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, a plant, plant tissue, or plant cell comprises a gene expression cassette comprising a *Zea mays* promoter and a *Zea mays* 3'-UTR. In an embodiment, a plant, plant tissue, or plant cell comprises a gene expression cassette comprising a) a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1 and b) a 3'-UTR, wherein the 3'-UTR is at least 80%, 85%, 90%, 91%, 92%, 93%, 94%, 95%, 96%, 97%, 98%, 99%, 99.5%, 99.8%, or 100% identical to SEQ ID NO:6.

In an embodiment, a plant, plant tissue, or plant cell comprises a gene expression cassette comprising a *Zea mays* promoter, *Zea mays* 5'-UTR, *Zea mays* intron, and a *Zea mays* 3'-UTR that are operably linked to a transgene. The promoter, intron, 5'-UTR, and 3'-UTR can be operably linked to different transgenes within a gene expression cassette when a gene expression cassette includes two or more transgenes. In an illustrative embodiment, a gene expression cassette comprises a *Zea mays* promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In an illustrative embodiment, a gene expression cassette comprises a *Zea mays* intron that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In an embodiment, a gene expression cassette comprises a *Zea mays* intron that is operably linked to a promoter, wherein the promoter is a *Zea mays* promoter of SEQ ID NO:1, or a promoter that originates from a plant (e.g., *Zea mays* ubiquitin 1 promoter), a virus (e.g., Cassava vein mosaic virus promoter) or a bacteria (e.g., *Agrobacterium tumefaciens* delta mas). In an illustrative embodiment, a gene expression cassette comprises a *Zea mays* 5'-UTR that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof. In an embodiment, a gene expression cassette comprises a *Zea mays* 5'-UTR that is operably linked to a promoter, wherein the promoter is a *Zea mays* promoter of SEQ ID NO:1, or a promoter that originates from a plant (e.g., *Zea mays* ubiquitin 1 promoter), a virus (e.g., Cassava vein mosaic virus promoter) or a bacteria (e.g., *Agrobacterium tumefaciens* delta mas). In an illustrative embodiment, a gene expression cassette comprises a *Zea mays* 3'-UTR that is operably linked to a transgene, wherein the 3'-UTR can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In an embodiment, transgene expression using methods described herein is specific to a plant's leaf tissues. In an embodiment, transgene expression includes more than one transgene expressed in the plant's leaf tissues. In an embodiment, a method of growing a transgenic plant as described herein includes leaf-specific transgene expression. In an embodiment, a method of expressing a transgene in a plant tissue or plant cell includes leaf-specific tissues and root-specific cells. In an embodiment, the leaf-specific expression includes maize leaf-specific expression.

In a further embodiment, transgene expression using methods described herein is expressed within above ground plant tissues (e.g., above ground plant tissues include leaf, husk, stem, and silk). In an embodiment, transgene expression includes more than one transgene expressed in above ground plant tissues. In an embodiment, a method of growing a transgenic plant as described herein includes above ground plant tissues transgene expression. In an embodiment, a method of expressing a transgene in a plant tissue or plant cell above ground plant tissues and above ground plant cells. In an embodiment, the above ground plant tissue expression includes maize above ground plant tissue expression.

In an embodiment, a plant, plant tissue, or plant cell comprises a vector comprising a *Zea mays* promoter, *Zea mays* 5'-UTR, *Zea mays* intron, and/or *Zea mays* 3'-UTR as disclosed herein. In an embodiment, a plant, plant tissue, or plant cell comprises a vector comprising a *Zea mays* promoter, *Zea mays* 5'-UTR, *Zea mays* intron, and/or *Zea mays* 3'-UTR as disclosed herein operably linked to a non-chlorophyll a/b transgene. In an embodiment, a plant, plant tissue, or plant cell comprises a vector comprising a gene expression cassette as disclosed herein. In an embodiment, a vector can be a plasmid, a cosmid, a bacterial artificial chromosome (BAC), a bacteriophage, or a virus.

In accordance with one embodiment a plant, plant tissue, or plant cell is provided wherein the plant, plant tissue, or plant cell comprises a non-endogenous *Zea mays* derived promoter sequence operably linked to a transgene, wherein the *Zea mays* promoter sequence comprises a sequence of SEQ ID NO:1 or a sequence having 90. 95, 98 or 99% sequence identity with SEQ ID NO:1. In one embodiment a plant, plant tissue, or plant cell is provided wherein the plant, plant tissue, or plant cell comprises SEQ ID NO: 1, or a sequence that has 90% sequence identity with SEQ ID NO: 1 operably linked to a non-chlorophyll a/b transgene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of maize, wheat, rice, sorghum, oats, rye, bananas, sugar cane, soybean, cotton, sunflower, and canola. In one embodiment the plant is *Zea mays*.

In one embodiment a plant, plant tissue, or plant cell is provided comprising SEQ ID NO:1, or a sequence that has 90, 95, 98 or 99% sequence identity with SEQ ID NO:1, operably linked to a transgene. In accordance with one embodiment the plant, plant tissue, or plant cell is a dicotyledonous or monocotyledonous plant or plant cell or tissue derived from a dicotyledonous or monocotyledonous plant. In one embodiment the plant is selected from the group consisting of maize, wheat, rice, sorghum, oats, rye, bananas, sugar cane, soybean, cotton, sunflower, and canola. In one embodiment the plant is *Zea mays*. In accordance with one embodiment the promoter sequence operably linked to a transgene is incorporated into the genome of the plant, plant tissue, or plant cell. In one embodiment the plant, plant tissue, or plant cell further comprises a 5' untranslated sequence comprising SEQ ID NO:4 or a sequence that has 90% sequence identity with SEQ ID NO:4, wherein the 5' untranslated sequence is inserted between, and operably linked to, said promoter and said transgene. In a further embodiment the plant, plant tissue, or plant cell further comprises an intron sequence inserted after the 5' untranslated sequence. In one embodiment the intron sequence is an intron sequence isolated from a chlorophyll a/b gene of *Zea mays*. In one embodiment the intron sequence comprises or consists of SEQ ID NO:2 or SEQ ID NO:3.

In one embodiment a plant, plant tissue, or plant cell is provided that comprises SEQ ID NO:1, or a sequence that has 90. 95, 98 or 99% sequence identity with SEQ ID NO:1, operably linked to the 5' end of a transgene and a 3' untranslated sequence comprising SEQ ID NO:6 or a sequence that has 90% sequence identity with SEQ ID NO:6, wherein the 3' untranslated sequence is operably linked to said transgene. In accordance with one embodiment the plant, plant tissue, or plant cell is a dicotyledonous or monocotyledonous plant or is a plant issue or cell derived from a dicotyledonous or monocotyledonous plant. In one embodiment the plant is selected from the group consisting of maize, wheat, rice, sorghum, oats, rye, bananas, sugar cane, soybean, cotton, sunflower, and canola. In one embodiment the plant is *Zea mays*. In accordance with one embodiment the promoter sequence operably linked to a transgene is incorporated into the genome of the plant, plant tissue, or plant cell. In one embodiment the plant, plant tissue, or plant cell further comprises a 5' untranslated sequence comprising SEQ ID NO:4 or a sequence that has 90% sequence identity with SEQ ID NO:4, wherein the 5' untranslated sequence is inserted between, and operably linked to, said promoter and said transgene. In a further embodiment the plant, plant tissue, or plant cell comprises an intron sequence inserted after the 5' untranslated sequence. In one embodiment the intron sequence is an intron sequence isolated from a chlorophyll a/b gene of *Zea mays*. In one embodiment the 5' 5' untranslated sequence consists of SEQ ID NO:4.

In an embodiment, a plant, plant tissue, or plant cell according to the methods disclosed herein can be a monocotyledonous plant. The monocotyledonous plant, plant tissue, or plant cell can be, but not limited to corn, rice, wheat, sugarcane, barley, rye, sorghum, orchids, bamboo, banana, cattails, lilies, oat, onion, millet, and triticale.

In an embodiment, a plant, plant tissue, or plant cell according to the methods disclosed herein can be a dicotyledonous plant. The dicotyledonous plant, plant tissue, or plant cell can be, but not limited to rapeseed, canola, Indian mustard, Ethiopian mustard, soybean, sunflower, and cotton.

With regard to the production of genetically modified plants, methods for the genetic engineering of plants are well known in the art. For instance, numerous methods for plant transformation have been developed, including biological and physical transformation protocols for dicotyledonous plants as well as monocotyledonous plants (e.g., Goto-Fumiyuki et al., *Nature Biotech* 17:282-286 (1999); Miki et al., Methods in Plant Molecular Biology and Biotechnology, Glick, B. R. and Thompson, J. E. Eds., CRC Press, Inc., Boca Raton, pp. 67-88 (1993)). In addition, vectors and in vitro culture methods for plant cell or tissue transformation and regeneration of plants are available, for example, in Gruber et al., Methods in Plant Molecular Biology and Biotechnology, Glick, B. R. and Thompson, J. E. Eds., CRC Press, Inc., Boca Raton, pp. 89-119 (1993).

One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed cells can also be identified by screening for the activities of any visible marker genes (e.g., the yfp, gfp, β-glucuronidase, luciferase, B or C1 genes) that may be present on the recombinant nucleic acid vectors. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) Next Generation Sequencing (NGS) analysis; 5) protein gel electrophoresis, Western blot techniques, immunoprecipitation, or enzyme-linked immunoassay (ELISA), where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, Northern blots of the RNA (e.g., mRNA) isolated from the tissues of interest. Typically, if the mRNA is present or the amount of mRNA has increased, it can be assumed that the corresponding transgene is being expressed. Other methods of measuring gene and/or encoded polypeptide activity can be used. Different types of enzymatic assays can be used, depending on the substrate used and the method of detecting the increase or decrease of a reaction product or by-product. In addition, the levels of polypeptide expressed can be measured immunochemically, i.e., ELISA, RIA, EIA and other antibody based assays well known to those of skill in the art, such as by electrophoretic detection assays (either with staining or Western blotting). As one non-limiting example, the detection of the AAD-1 (aryloxyalkanoate dioxygenase; see WO 2005/107437) and PAT (phosphinothricin-N-acetyl-transferase), proteins using an ELISA assay is described in U.S. Patent Publication No. 20090093366 which is herein incorporated by reference in its entirety. The transgene may be selectively expressed in some cell types or tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

While the invention has been described with reference to specific methods and embodiments, it will be appreciated that various modifications and changes may be made without departing from the invention.

EXAMPLES

Example 1

Identification of High Expressing Regulatory Elements

Novel *Zea mays* regulatory elements were identified via a transcriptional profiling approach by using next generation sequencing (NGS). These regulatory elements were then isolated, and cloned to characterize the expression profile of the regulatory elements for use in transgenic plants. Transgenic maize lines stably transformed with a cry34Ab1 reporter gene isolated from *Bacillus thuringiensis*, a phiyfp reporter gene, and an aad-1 selectable marker gene were produced and the transgene expression levels and tissue specificity was assessed. As such novel *Zea mays* regulatory elements were identified and characterized. Disclosed for the first time are promoter and 3'-UTR regulatory elements for use in gene expression constructs.

Maize tissues were obtained from plants grown to different stages of plant growth and development for transcriptional profiling in order to identify and select regulatory elements of native maize genes with desired expression profiles for use in gene expression constructs. For example, tissue samples from 3 stages of leaf (V4 (duplicate), V12 and R3) and root (V4 and V12 nodal and fibrous tissues) development, pollen, silk, cob, immature kernel, husk and stem (V4 and R1) were collected. Total mRNA was isolated from all of the above described tissues and high quality mRNA in desired quantities were obtained.

cDNA libraries were prepared from each of the mRNA samples and high-throughput sequencing was completed using an Illumina HiSeq® 2000 (Illumina Inc., San Diego, Calif.). In addition, the Illumina TruSeq® RNA sample preparation kit was used according to the manufacturer's recommended protocol for RNAseq sample preparation. In brief, 5 µg of total RNA was purified using poly-T oligo-attached magnetic beads followed by fragmentation into smaller pieces (about 200 bp average length) using divalent cations under high temperature. SuperScript® II reverse transcriptase and random primers were then used to copy the fragmented mRNA into first strand cDNA. The cDNA was further converted into double stranded cDNA (ds cDNA) using DNA polymerase I and RNase H. The double stranded cDNA fragments then went through end repair, A-tailing, and then ligation to indexed Illumina paired-end (PE) adapters. Lastly, library products were cleaned up and enriched with 15 cycles of PCR and purified. The enriched libraries were normalized to a concentration of 2 nM, denatured with sodium hydroxide, and diluted to 12 pM in hybridization buffer for loading onto a single lane of a HiSeq® flow cell. Cluster generation, primer hybridization and sequencing reactions were carried out according to Illumina's recommended protocol.

The sequencing reads were then filtered to remove low quality reads. About 99.9% of the sequencing reads were retained after filtering. The sequencing reads were aligned to the annotated Zea mays c.v. B73 genome available in the maizeGDB. Sequencing reads that mapped onto the maize genome at more than one locus were discarded to avoid confusion in identification of the high expressing genes and their further characterization. This step led to alignment of >70% sequencing reads from each of the samples to the maize genome. The quantitative gene expression unit of fragments per kilobase of exon per million fragments mapped or FPKM values were used to rank genes for stable transformation testing that matched a desirable expression pattern for use in gene expression constructs. Highly expressed genes in maize were prioritized for testing in stable transgenic lines (FIG. 1).

Example 2

Selection of Novel Regulatory Elements from Zea mays Sequence

The promoter, intron, 5'-UTR, and 3'-UTR sequences were extracted from a Zea mays gene sequence that ranked highly for expression through the transcriptional profiling approach. The native sequence of the Zea mays gene, from the Zea may c.v. B73 genome, is provided as SEQ ID NO:7. The 379 bp Zea mays promoter sequence (SEQ ID NO:1) is provided. In addition to the 119 bp Zea mays intron sequence (SEQ ID NO:2), and the 91 bp Zea mays intron (2) sequence (SEQ ID NO:3) are provided as fragments making up SEQ ID NO:7. Furthermore, the 152 bp Zea mays 5'-UTR sequence (SEQ ID NO:4) is provided. Finally, the 295 bp Zea mays 3'-UTR sequence (SEQ ID NO:6) is also provided.

Example 3

Construct Design

The DNA elements were synthesized and cloned into entry vectors. The Zea mays promoter, intron, and 5'-UTR (SEQ ID NO:5), cry34Ab1 (reporter gene from B. thuringiensis), and the Solanum tuberosum protease inhibitor gene II 3' UTR (StPinII 3'-UTR v2; An et al., (1989) *Plant Cell* 1; 115-22) were amplified with primers containing a minimum 15 bp overlapping homology to their flanking DNA element within the donor construct. All fragments were gel purified. All three fragments along with an entry vector backbone, pENTR11, were assembled in a directional order through a Geneart® Seamless cloning reaction (Invitrogen, Carlsbad, Calif.). The resulting gene expression cassette contained the cry34Ab1 transgene operably linked to the 3' end of the *Zea mays* promoter, intron, and 5'-UTR (SEQ ID NO:5). A Gateway® LR Clonase® (Invitrogen) reaction was then performed with the resulting entry plasmid, pDAB114404, and a destination vector, pDAB104153, leading to a final expression vector, pDAB114411. The destination vector contained a selectable marker cassette comprised of an aad-1 gene driven by the *Zea mays* ubiquitin-1 promoter (Christensen et al., (1992) *Plant Molecular Biology* 18; 675-689) and terminated by a maize lipase 3'-UTR (U.S. Pat. No. 7,179,902). The resulting construct, pDAB114411 is a heterologous expression construct that contains an aad-1 gene expression cassette and a cry34Ab1 gene expression cassette (FIG. 2).

A second entry vector, pDAB116024, cassette was assembled with Geneart® Seamless cloning reaction by replacing the cry34Ab1 gene with a phiYFP reporter gene (Shagin et al., (2004) *Mol Biol Evol* 21; 841-50) containing a *Solanum tuberosum* LS1 intron (St-LS1; Vancanneyt G F et al., (1990) *Mol Gen Genet* 220(2):245-250) and replacing the StPinII 3'-UTR with the novel 295 bp 3'-UTR sequence (SEQ ID NO:6) obtained from *Zea mays*. Both the promoter, intron, and 5'-UTR (SEQ ID NO:5) and 3'-UTR (SEQ ID NO:6) elements were derived from the same native gene of *Zea mays*. The resulting gene expression cassette contained the phiYFP transgene operably linked to the 3' end of the *Zea mays* promoter, intron, and 5'-UTR (SEQ ID NO:5). Following a Gateway reaction with a destination vector, pDAB104153, a final expression construct, pDAB116038, was assembled. The destination vector contained a selectable marker cassette comprised of an aad-1 gene driven by the *Zea mays* ubiquitin-1 promoter (Christensen et al., (1992) *Plant Molecular Biology* 18; 675-689) and terminated by a maize lipase 3'-UTR (U.S. Pat. No. 7,179,902). The resulting construct, pDAB116038 is a heterologous expression construct that contains an aad-1 gene expression cassette and a phiYFP gene expression construct (FIG. 3).

A negative control construct, pDAB101556, was assembled containing a yellow fluorescence protein (YFP) reporter gene instead of the cry34Ab1 gene (FIG. 4) and the same aad-1 expression cassette as present in pDAB114411. A positive control construct, pDAB108746, was built comprised of the *Zea mays* ubiquitin-1 promoter and *Solanum tuberosum* protease inhibitor gene II 3' UTR (StPinII 3'-UTR v2; An et al., (1989) *Plant Cell* 1; 115-22) controlling the expression of the cry34Ab1 gene (FIG. 5). The aad-1 cassette was the same as present in pDAB114411. Another positive control construct, pDAB113121, was built comprised of the *Zea mays* ubiquitin-1 promoter and *Solanum tuberosum* protease inhibitor gene II 3' UTR (StPinII 3'-UTR v2; An et al., (1989) *Plant Cell* 1; 115-22) controlling the expression of the phiYFP gene containing an St-LS1 intron (FIG. 6). The aad-1 cassette was the same as present in pDAB116038.

Example 4

Plant Transformation and Molecular Confirmation

Transformation of *Agrobacterium tumefaciens*:

The binary expression vectors were transformed into *Agrobacterium tumefaciens* strain DAt13192 (RecA deficient ternary strain) (Int. Pat. Pub. No. WO2012016222). Bacterial colonies were selected, and binary plasmid DNA was isolated and confirmed via restriction enzyme digestion.

*Agrobacterium* Culture Initiation:

*Agrobacterium* cultures were streaked from glycerol stocks onto AB minimal medium (Gelvin, S., 2006, *Agrobacterium* Virulence Gene Induction, in Wang, K., ed., *Agrobacterium* Protocols Second Edition Vol. 1, Humana Press, p. 79; made without sucrose and with 5 g/L glucose and 15 g/L Bacto™ Agar) and incubated at 20° C. in the dark for 3 days. *Agrobacterium* cultures were then streaked onto a plate of YEP medium (Gelvin, S., 2006, *Agrobacterium* Virulence Gene Induction, in Wang, K., ed., *Agrobacterium* Protocols Second Edition Vol. 1, Humana Press, p. 79) and incubated at 20° C. in the dark for 1 day.

On the day of an experiment, a mixture of Inoculation medium (2.2 g/L MS salts, 68.4 g/L sucrose, 36 g/L glucose, 115 mg/L L-proline, 2 mg/L glycine, 100 mg/L myo-Inositol, 0.05 mg/L nicotinic acid, 0.5 mg/L pyridoxine HCl, 0.5 mg/L thiamine HCl) and acetosyringone was prepared in a volume appropriate to the size of the experiment. A 1 M stock solution of acetosyringone in 100% dimethyl sulfoxide was added to the Inoculation medium to make a final acetosyringone concentration of 200 µM.

For each construct, 1-2 loops of *Agrobacterium* from the YEP plate were suspended in 15 ml of the inoculation medium/acetosyringone mixture inside a sterile, disposable, 50 ml centrifuge tube and the optical density of the solution at 600 nm ($O.D._{600}$) was measured in a spectrophotometer. The suspension was then diluted down to 0.25-0.35 $O.D._{600}$ using additional Inoculation medium/acetosyringone mixture. The tube of *Agrobacterium* suspension was then placed horizontally on a platform shaker set at about 75 rpm at room temperature for between 1 and 4 hours before use.

Maize Transformation:

Experimental constructs were transformed into maize via *Agrobacterium*-mediated transformation of immature embryos isolated from the inbred line, *Zea mays* c.v. B104. The method used is similar to those published by Ishida et al., (1996) Nature Biotechnol 14:745-750 and Frame et al., (2006) Plant Cell Rep 25: 1024-1034, but with several modifications and improvements to make the method amenable to high-throughput transformation. An example of a method used to produce a number of transgenic events in maize is given in U.S. Pat. App. Pub. No. US 2013/0157369 A1, beginning with the embryo infection and co-cultivation steps. Transfer and establishment of $T_0$ plants in the greenhouse:

Transgenic plants were transferred on a regular basis to the greenhouse. Plants were transplanted from Phytatrays™ to small pots (T. O. Plastics, 3.5" SVD, 700022C) filled with growing media (Premier Tech Horticulture, ProMix BX) and covered with humidomes to help acclimate the plants. Plants were placed in a Conviron™ growth chamber (28° C./24° C., 16-hour photoperiod, 50-70% RH, 200 µmol $m^{-2}$ $s^{-1}$ light intensity) until reaching V3-V4 stage. This aided in acclimating the plants to soil and harsher temperatures. Plants were then moved to the greenhouse (Light Exposure Type: Photo or Assimilation; High Light Limit: 1200 µmol $m^{-2}$ $s^{-1}$ photosynthetically active radiation (PAR); 16-hour day length; 27° C. Day/24° C. Night) and transplanted from the small pots to 5.5 inch pots. Approximately 1-2 weeks after transplanting to larger pots the plants were sampled for bioassay. One plant per event was assayed.

Example 5

Molecular Confirmation of Transgenic Plants/Events

Putative transgenic maize plants were sampled at the V2-3 leaf stage for transgene presence using cry34Ab1 and AAD-1 quantitative PCR assays. Total DNA was extracted from the leaf samples using MagAttract® DNA extraction kit (Qiagen) as per manufacturer's instructions.

To detect the genes-of-interest, gene-specific DNA fragments were amplified with TaqMan® primer/probe sets containing a FAM-labeled fluorescent probe for the cry34Ab1 gene and a HEX-labeled fluorescent probe for the endogenous invertase reference gene control. The following primers were used for the cry34Ab1 and invertase endogenous reference gene amplifications.

```
Cry34Ab1 Primers/probes:
Forward Primer:
TQ.8v6.1.F:
                                          (SEQ ID NO: 8)
GCCATACCCTCCAGTTG Reverse Primer:
TQ.8v6.1.R:
                                          (SEQ ID NO: 9)
GCCGTTGATGGAGTAGTAGATGG Probe:
TQ.8v6.1.MGB.P:
                                         (SEQ ID NO: 10)
5'-/56-FAM/CCGAATCCAACGGCTTCA/MGB Invertase Primers:
Forward Primer:
InvertaseF:
                                         (SEQ ID NO: 11)
TGGCGGACGACGACTTGT Reverse Primer:
InvertaseR:
                                         (SEQ ID NO: 12)
AAAGTTTGGAGGCTGCCGT InvertaseProbe:
                                         (SEQ ID NO: 13)
5'-/5HEX/CGAGCAGACCGCCGTGTACTT/3BHQ_1/-3'
```

Next, the PCR reactions were carried out in a final volume of 10 µl reaction containing 5 µl of Roche LightCycler® 480 Probes Master Mix (Roche Applied Sciences, Indianapolis, Ind.); 0.4 µl each of TQ.8v6.1.F, TQ.8v6.1.R, InvertaseF, and InvertaseR primers from 10 µM stocks to a final concentration of 400 nM; 0.4 µl each of TQ.8v6.1.MGB.P and Invertase Probes from 5 µM stocks to a final concentration of 200 nM, 0.1 µl of 10% polyvinylpyrrolidone (PVP) to final concentration of 0.1%; 2 µl of 10 ng/µl genomic DNA and 0.5 µl water. The DNA was amplified in a Roche LightCycler® 480 System under the following conditions: 1 cycle of 95° C. for 10 min; 40 cycles of the following 3-steps: 95° C. for 10 seconds; 58° C. for 35 seconds and 72° C. for 1 second, and a final cycle of 4° C. for 10 seconds. The cry34Ab1 copy number was determined by comparison of Target (gene of interest)/Reference (Invertase gene) values for unknown samples (output by the LightCycler® 480) to Target/Reference values of cry34Ab1 copy number controls.

The detection of the AAD-1 gene was carried out as described above for the cry34Ab1 gene using the invertase endogenous reference gene. The AAD-1 primer sequences were as follows;

```
AAD1 Forward Primer:
                                    (SEQ ID NO: 14)
TGTTCGGTTCCCTCTACCAA AAD1 Reverse Primer:
                                    (SEQ ID NO: 15)
CAACATCCATCACCTTGACTGA AAD1 Probe:
                                    (SEQ ID NO: 16)
5'-FAM/CACAGAACCGTCGCTTCAGCAACA-MGB/BHQ-3'.
```

The detection of the PhiYFP gene was carried out as described above for the cry34Ab1 gene using the invertase endogenous reference gene. The PhiYFP primer sequences were as follows;

```
PhiYFP v3 Forward Primer:
                                    (SEQ ID NO: 17)
CGTGTTGGGAAAGAACTTGGA PhiYFP v3 Reverse Primer:
                                    (SEQ ID NO: 18)
CCGTGGTTGGCTTGGTCT PhiYFP v3 Probe:
                                    (SEQ ID NO: 19)
5'FAM/CACTCCCCACTGCCT/MGB_BHQ_1/3'.
```

Finally, the $T_0$ plants containing the gene of interest were sampled at V4-5 for Cry34Ab1, PhiYFP, and AAD-1 leaf ELISA assays. Four leaf punches were sampled. Another set of plants were sampled at V4-5 for the entire root mass for both the protein ELISA assays. Leaf and root Cry34Ab1 (Agdia, Inc., Elkart, Ind.) and AAD-1 (Acadia BioScience) ELISA assays were performed as per the manufacturer's instructions.

The PhiYFP ELISA was completed as follows. Plates were coated with monoclonal anti-YFP capture antibody (Origene; Rockvile, Md.). The monoclonal anti-YFP capture antibody was diluted in PBS at a concentration of 1 µg/ml, and 150 µl of solution was added to the wells of the plates and incubated overnight at 4° C. Next, the plates were warmed to room temperature for 20 to 30 minutes. The plates were washed four times with 350 µl of wash buffer (1×PBS and 0.5% Tween 20). Then 200 µl of blocking buffer was aliquoted to the plates, and the plates were incubated at 37° C. for at least one hour. The plates were washed four times with 350 µl of wash buffer (1×PBS and 0.5% Tween 20).

Standards of recombinantly expressed PhiYFP (Evrogen; Moscow, Russia) were added to the wells in serial dilutions. The standards were initially provided at a concentration of 0.0313 ng/ml to 2 ng/ml. Next, the plates were placed on a shaker and incubated at room temperature. The plates were washed four times with 350 µl of wash buffer (1×PBS and 0.5% Tween 20). The primary rabbit anti-PhiYFP polyclonal antibody (Evrogen: Moscow, Russia) was reduced in concentration to 1 µg/ml and added to the plates. Next, the plates were placed on a shaker and incubated at room temperature. The plates were washed four times with 350 µl of wash buffer (1×PBS and 0.5% Tween 20). The secondary anti-rabbit antibody horseradish peroxidase (Pierce; Rockford, Ill.) was added to the plates. Next, the plates were placed on a shaker and incubated at room temperature. The plates were washed four times with 350 µl of wash buffer (1×PBS and 0.5% Tween 20). Finally, Pierce 1 Step Ultra TMB ELISA, substrate for horseradish peroxidase labeled antibody, was added to the wells and gently shaken. The results were quantitated with a spectrophotometer.

The Cry34Ab1 leaf ELISA assays were expressed as $ng/cm^2$, while the root ELISA results were expressed as parts per million (or ng protein per mg total plant protein). Total root protein assays were carried out with the Bradford detection method as per the manufacturer's instructions.

$T_0$ plants were selfed and crossed to Zea mays c.v. B104 non-transgenic transformation lines to obtain $T_1$ seed. Five-six transgenic lines or events of each of the test regulatory element constructs were advanced for $T_1$ protein and RNA gene expression studies and then to $T_2$ seed production. Accordingly, 30-40 $T_1$ seed of each of the events were sown; seedlings were sprayed with AssureII® at the V2-3 stage of development to kill non-transgenic segregants. The transgenic plants were sampled at multiple stages of plant development for Cry34Ab1, PhiYFP, and AAD-1 ELISA as follows: leaf (V4, V12 and R3); root (V4 and R1); stem (R1); pollen (R1); silk (R1); husk (R3); immature kernel (R3); and cob (R3). All tissues were isolated and placed in tubes embedded in dry ice; which were then transferred to −80° C. Frozen tissues were lyophilized prior to protein extraction for ELISA.

Putative transgenic $T_1$ plants containing cry34Ab1, PhiYFP and AAD-1 transgenes were sampled at V4-5 for the leaf ELISA assays. Four leaf punches were sampled. The leaf punches were placed into a tube and a single ⅛" stainless steel bead (Hoover Precision Products, Cumming, Ga., USA) was added to each 1.2 ml tube containing 300 µl extraction buffer (1×PBST supplemented with 0.05% Tween 20 and 0.5% BSA). The samples were processed in a Genogrinder™ (SPEX SamplePrep, Metuchen, N.J.) at 1,500 rpm for 4 minutes. The samples were centrifuged at 4,000 rpm for 2 minutes in a Sorvall Legend XFR™ centrifuge. Next, an additional 300 µl of extraction buffer was added and the samples were processed once more in a Genogrinder™ at 1,500 rpm for 2 minutes. The samples were centrifuged once more at 4,000 rpm for 7 minutes. Finally, the supernatant was collected and ELISA assays were completed at different dilutions along with the protein standards using the commercially available Cry34Ab1 (Agdia, Inc.) and AAD-1 (Acadia BioScience, LLC) ELISA assay kits, per the manufacturer's instructions.

Protein extraction for various tissue type ELISAs was carried out by grinding the lyophilized tissue in a paint shaker for 30 seconds. For tissues needing further grinding, the grinding step was repeated for another 30 seconds. Garnet powder was added to cover the curved portion at the bottom of the tube. The coarsely ground tissue was transferred to 2 ml tubes and filled up to the 0.5 ml mark. One ceramic ball was added to each tube, as was 0.6 ml of the partial extraction buffer (200 µl of protease inhibitor cocktail, 200 µl of 500 mM EDTA, 15.5 mg DTT powder and PBST to 20 ml). All of the tubes were kept on ice for 10 minutes. The cold tubes were transferred to the 2 ml holder of the Genogrinder®. The samples were ground twice for 30 seconds with a 5 minute cooling on ice in between. Next, 40 µl of 10% Tween®-20 and 300 µl extraction buffer were added to the samples. The samples were ground for another 30 seconds with 5 minutes of cooling in between. Finally, each sample was centrifuged at 13,000 rpm for 7 minutes, and the supernatant was carefully transferred to a new tube to collect the extract. The extract was re-suspended in the extraction buffer and was diluted as needed for ELISA assays.

Example 6

$T_0$ Transgenic Plant Expression Screening

The ELISA results indicated that the regulatory elements isolated from *Zea mays* drove leaf tissue-preferred expression of cry34Ab1 in $T_0$ events that were transformed with construct, pDAB114411. Lower expression of Cry34Ab1 by the *Zea mays* regulatory elements were observed in the roots (Tables 3 and 4), compared to pDAB108746 positive control, of the $T_0$ events that were transformed with construct, pDAB114411. The events produced from the control construct pDAB108746 expressed Cry34Ab1 in both leaf and root tissues. There was no Cry34Ab1 leaf expression observed in plant events transformed with the control construct, pDAB101556 that did not contain the cry34Ab1 gene. All constructs expressed the AAD-1 protein in both root and leaf tissues.

The results of the PhiYFP ELISA indicated that $T_0$ transgenic events transformed with construct pDAB116038, which expressed a phiYFP transgene terminated by the *Zea mays* 3'-UTR regulatory element of the same gene as the promoter, produced high levels of PhiYFP protein in leaf tissues. The expression levels of the PhiYFP protein in the pDAB116038 events were higher than the expression levels of PhiYFP protein produced in transgenic events transformed with a positive control construct pDAB113121, which expressed a phiYFP transgene terminated by the StPinII 3'-UTR regulatory element (Table 5). Both constructs, pDAB116038 and pDAB113121, expressed the AAD-1 protein in both root and leaf tissues. Furthermore, transgenic pDAB116038 events produced with the *Zea mays* 3'-UTR resulted in increased expression of PhiYFP protein as compared to expression of Cry34Ab1 protein produced from cry34Ab1 transgenic events transformed with pDAB114411 and pDAB108746, both of which contained a StPinII 3'-UTR.

TABLE 3

$T_0$ ELISA results showing cry34Ab1 and aad-1 transgene expression in V4-V6 maize leaves of various construct events.

| Construct Name | No. of Events Analyzed | Mean Cry34Ab1 (ng/cm$^2$) | Cry34Ab1 Standard Deviation | Mean AAD-1 (ng/cm$^2$) | AAD-1 Standard Deviation |
|---|---|---|---|---|---|
| Experiment 1 | | | | | |
| pDAB101556 | 6 | 0 | 0 | 304 | 229 |
| pDAB108746 | 5 | 173 | 75 | 247 | 146 |
| pDAB114411 | 15 | 71 | 41 | 226 | 157 |
| Experiment 2 | | | | | |
| pDAB101556 | 6 | 0 | 0 | 304 | 229 |
| pDAB108746 | 18 | 129 | 79 | 173 | 96 |
| pDAB114411 | 30 | 64 | 40 | 233 | 151 |

TABLE 4

$T_0$ ELISA assay results showing cry34Ab1 and aad-1 transgene expression in V4-6 maize roots of various construct events.

| Construct Name | No. of Events Analyzed | Mean Cry34Ab1 (ng/mg) | Cry34Ab1 Standard Deviation | Mean AAD-1 (ng/mg) | AAD-1 Standard Deviation |
|---|---|---|---|---|---|
| Experiment 1 | | | | | |
| pDAB101556 | 1 | 0 | 0 | 871 | 0 |
| pDAB108746 | 2 | 970 | 1243 | 445 | 97 |
| pDAB114411 | 5 | 72 | 97 | 399 | 290 |
| Experiment 2 | | | | | |
| pDAB101556 | 2 | 0 | 0 | 1204 | 798 |
| pDAB108746 | 3 | 2938 | 2653 | 538 | 304 |
| pDAB114411 | 1 | 76 | 33 | 1132 | 592 |

TABLE 5

$T_1$ ELISA assay results showing cry34Ab1 and aad-1 transgene expression in multiple tissue types of maize in various construct events.

| Construct No. | Tissue analyzed | Total events analyzed | Total samples analyzed | Mean Cry34Ab1 (ng/mg) | Standard Deviation | Mean AAD-1 (ng/mg) | Standard Deviation |
|---|---|---|---|---|---|---|---|
| pDAB101556 | Leaf V4 | 1 | 13 | 1 | 0 | 497 | 161 |
| pDAB114411 | Leaf V4 | 3 | 31 | 753 | 199 | 1133 | 688 |
| pDAB114411 | Leaf V12 | 3 | 12 | 1010 | 211 | 1698 | 799 |
| pDAB114411 | Leaf R3 | 3 | 9 | 3260 | 1068 | 2133 | 1031 |

TABLE 5-continued

T₁ ELISA assay results showing cry34Ab1 and aad-1 transgene expression in multiple tissue types of maize in various construct events.

| Construct No. | Tissue analyzed | Total events analyzed | Total samples analyzed | Mean Cry34Ab1 (ng/mg) | Standard Deviation | Mean AAD-1 (ng/mg) | Standard Deviation |
|---|---|---|---|---|---|---|---|
| pDAB101556 | Root V4 | 1 | 3 | 4 | 3 | 2722 | 234 |
| pDAB114411 | Root V4 | 3 | 8 | 49 | 20 | 3112 | 2004 |
| pDAB114411 | cob | 2 | 10 | 156 | 67 | 7431 | 3056 |
| pDAB114411 | silk | 2 | 6 | 2069 | 489 | 12495 | 3216 |
| pDAB114411 | kernel | 2 | 8 | 39 | 32 | 4823 | 1854 |
| pDAB114411 | stem | 2 | 6 | 1921 | 545 | 12690 | 4500 |
| pDAB114411 | husk | 2 | 10 | 949 | 297 | 3337 | 1130 |
| pDAB114411 | pollen | 2 | 5 | 35 | 10 | 2397 | 1508 |

TABLE 6

ELISA assay results depicting phiYFP and aad-1 transgene expression in T₀ (V4-6) maize leaves when a native 3' UTR present in pDAB116038 controlled the phiYFP gene expression.

| Construct No. | No. of Events Analyzed | Mean YFP (ng/mg) | YFP Standard Deviation | Mean AAD-1 (ng/mg) | AAD-1 Standard Deviation |
|---|---|---|---|---|---|
| pDAB116038 | 18 | 407 | 286 | 350 | 365 |
| pDAB113121 | 10 | 244 | 303 | 91 | 46 |

TABLE 7

ELISA assay results depicting phiYFP and aad-1 transgene expression in T₁ (V4-6) maize leaves when a native 3' UTR present in pDAB116038 controlled the phiYFP gene expression.

| Sample ID | Leaf Stage | Total events analyzed | Total plants analyzed | Mean PhiYFP (ng/mg) | STD | Mean AAD1 (ng/mg) | STD |
|---|---|---|---|---|---|---|---|
| pDAB108746 | Leaf V4 | 1 | 10 | 6 | 0 | 136 | 66 |
| pDAB116038 | Leaf V4 | 3 | 22 | 975 | 113 | 241 | 293 |
| pDAB108746 | Leaf V12 | 1 | 3 | 6 | 0 | 347 | 63 |
| pDAB116038 | Leaf V12 | 3 | 9 | 769 | 268 | 728 | 463 |
| pDAB108746 | Leaf R3 | 1 | 3 | 6 | 0 | 1009 | 218 |
| pDAB 116038 | Leaf R3 | 3 | 9 | 185 | 47 | 2216 | 1162 |

As such novel maize regulatory elements isolated from *Zea mays* were identified and characterized. Disclosed for the first time are promoter (SEQ ID NO:5) and 3'-UTR (SEQ ID NO:6) regulatory elements for use in gene expression constructs.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention. The following examples are provided to illustrate certain particular features and/or embodiments. The examples should not be construed to limit the disclosure to the particular features or embodiments exemplified.

What is claimed is:

1. A nucleic acid vector comprising a promoter operably linked to a heterologous nucleic acid sequence,
   wherein said promoter comprises SEQ ID NO: 5,
   wherein the nucleic acid vector further comprises a 3' untranslated sequence comprising SEQ ID NO: 6, and wherein the 3' untranslated sequence is operably linked to said heterologous nucleic acid sequence.

2. The nucleic acid vector of claim 1, wherein said promoter is less than 3kb in length.

3. The nucleic acid vector of claim 1, wherein said promoter consists of SEQ ID NO: 5.

4. The nucleic acid vector of claim 1, wherein said heterologous nucleic acid sequence is a transgene or small RNA.

5. The nucleic acid vector of claim 4, wherein the transgene encodes a selectable marker or a gene product conferring insecticidal resistance, herbicide tolerance, nitrogen use efficiency, water use efficiency, or nutritional quality.

6. A plant comprising SEQ ID NO: 5 operably linked to a heterologous transgene, and wherein the plant further comprises a 3' untranslated sequence comprising SEQ ID NO: 6, wherein the 3' untranslated sequence is operably linked to said transgene.

7. The plant of claim 6, wherein said plant is selected from the group consisting of *Zea mays*, wheat, rice, sorghum, oats, rye, bananas, sugar cane, soybean, cotton, sunflower, Arabidopsis, tobacco, and canola.

8. The plant of claim 6, wherein the plant is *Zea mays*.

9. The plant of claim 6, wherein the transgene is inserted into the genome of the plant.

\* \* \* \* \*